US006013779A

United States Patent [19]
Wong et al.

[11] Patent Number: 6,013,779
[45] Date of Patent: Jan. 11, 2000

[54] PROCESS FOR PREPARATION OF GLYCOSIDES OF TUMOR-ASSOCIATED CARBOHYDRATE ANTIGENS

[75] Inventors: Ting Chi Wong; R. Rao Koganty, both of Edmonton, Canada

[73] Assignee: Biomira, Inc., Edmonton, Canada

[21] Appl. No.: 08/819,994

[22] Filed: Mar. 18, 1997

Related U.S. Application Data

[63] Continuation of application No. 08/235,954, May 2, 1994, abandoned.
[51] Int. Cl.$^7$ ...................................................... C07H 1/00
[52] U.S. Cl. ..................... 536/18.6; 536/4.1; 536/18.5; 530/322; 530/350
[58] Field of Search .................................. 536/18.6, 4.1; 530/322, 350

[56] References Cited

U.S. PATENT DOCUMENTS

| | | | |
|---|---|---|---|
| 3,598,865 | 8/1971 | Lew | 536/4.1 |
| 4,137,401 | 1/1979 | Lemieux et al. . | |
| 4,195,174 | 3/1980 | Lemieux et al. . | |
| 4,308,376 | 12/1981 | Lemieux et al. . | |
| 4,356,170 | 10/1982 | Jennings et al. . | |
| 4,362,720 | 12/1982 | Lemieux et al. . | |
| 4,442,284 | 4/1984 | Kolar et al. . | |
| 4,536,336 | 8/1985 | Kishi | 280/351.1 |
| 4,563,445 | 1/1986 | Feizi et al. . | |
| 4,794,176 | 12/1988 | Lemieux et al. . | |
| 4,866,041 | 9/1989 | Lemieux et al. . | |
| 4,866,045 | 9/1989 | Tieman . | |
| 4,935,503 | 6/1990 | Naicker et al. . | |
| 5,030,621 | 7/1991 | Bystryn . | |
| 5,034,516 | 7/1991 | Roy et al. | 536/4.1 |
| 5,055,562 | 10/1991 | Koganty . | |
| 5,079,353 | 1/1992 | Ratcliffe et al. . | |

OTHER PUBLICATIONS

Tam, Synthetic Peptide Vaccine Design: Synthesis and Properties of a High–Density Multiple Antigenic Peptide System, Proc. Natl. Acad. Sci. USA, vol. 85, pp. 5409–5413, Aug. 1988.
Paulsen et al, Synthese Der glycopeptide O–β–D–Galactopyranosyl–(1→3)–O–(2–Acetamido–2–Desoxy–α–D Galactopyranosyl)–(1→3)–L–Serin Und–L–Threonin, Carbohydrate Research, vol. 109, pp. 89–107, 1982.
Bencomo et al, Synthesis of Glycopeptides having Clusters of O–Glycosylic Disaccharide Chains [β–D–Gal–(1→3)–α–D–GalNAc] Located at Vicinal Amino Acid Residues of the Peptide Chain, Carbohydrate Reasearch, vol. 116, pp. C9–C12, 1983.
Marra et al, Acetylation of N–Acetylneuraminic Acic and its Methyl Ester, Carbohydrate Research, vol. 190, pp. 317–322, 1989.
Dubois et al, Colorimetric Method for Determination of Sugars and Related Substances, Analytical Chemistry, vol. 28, no. 3, pp. 350–356, Mar. 1956.
Iijima et al, Synthesis of a Mucin–Type o–Glycosylated Amino Acid, β–Ga(1—3)–[α–Neu5Ac–(2—6)]–α–Gal–Nac–(1—3)–Ser, Carbohydrate Research, vol. 186, pp. 95–106, 1989.
Fung et al, Active Specific Immunotherapy of a Murine Mammary Adenocarcinoma Using a Synthetic Tumor–Associated Glycoconjugate, Cancer Research, vol. 50, pp. 4308–4314, Jul. 15, 1990.
Posnett et al, A Novel Method for Producing Anti–Peptide Antibodies, The Journal of Biological Chemistry, vol. 265, No. 4, pp. 1719–1725, Feb. 5, 1985.
Paulsen, Synthesis of Complex Oligosaccharide Chains of Glycoproteins, Haworth Memorial Lecture, pp. 15–45, Mar. 28, 1983.
Paulsen, Strategies in Oligosaccharide Synthesis, Institute of Organic Chemistry, pp. 317–335, 1984.
Schmidt, New Methods for the Synthesis of Glycosides and Oligosaccharides—Are There Alternatives to the Koenigs–Knorr Method?, Angew. Chem. Int. Ed. Engl., vol. 25, pp. 212–234, 1986.
Flowers, Chemical Synthesis of Oligosaccharides, Methods of Enzymology, vol. 138, pp. 359–405.
Springer, T and Tn, General Carcinoma Autoantigens, Science, vol. 224, pp. 1198–1206, Jun. 15, 1984.
Paulsen et al, Synthese Einer Disaccharideinheit Aus N–Acetylneuraminsaure und 2–Acetamido–2–Desoxy–D–Galactose, Carbohydrate Research, vol. 137, pp. 63–77, 1985.
Hull et al, Oligosaccharide Differences in the DF3 Sialomucin Antigen from Normal Human Milk and the BT–20 Human Breast Carcinoma Cell Line, Cancer Communications, vol. 1, No. 4, pp. 261–267, 1989.
Paulsen et al, Synthese von 0–(5–Acetamido–3, 5–Didesoxy–D–Glycero–a–D–Galacto–2–nonulopyranosylonsaure)–(2—3)–O–β–D–Galactopyranosyl–(1—3)–2 Acetamido–2–Desoxy–D–Galactopyranose, Carbohydrate Research, vol. 175, pp. 283–293, 1988.
Lemieux et al, The Azidonitration of Tri–O–Acetyl–D–Galactal, Can. J. Chem., vol. 57, pp. 1244–1251, 1979.
Paulsen et al, Synthese a–Glycosidisch Verknupfter Disaccharide Der 2–Amino–2–Desoxy–D–Galactopyranose, Chem. Ber., vol. 111, 1978.
Roussel et al, The Complexity of Mucins, Biochimie, vol. 70, pp. 1471–1482, 1988.

(List continued on next page.)

*Primary Examiner*—Elli Peselev
*Attorney, Agent, or Firm*—Iver P. Cooper

[57] ABSTRACT

Glycoconjugate antigens are prepared by preparing a hapten glycoside, especially an alpha glycoside prepared by the Fischer method, with an olefinic aglycon moiety, especially one having a non-terminal double bond, ozonolyzing the hapten glycoside with an olefinic aglycon moiety having a non-terminal double bond to form a hapten-glycoside derivative, preferably without producing Germaldehyde as a byproduct removing by-products of ozonolysis, and conjugating the hapten-glycoside derivative to a carrier.

23 Claims, 8 Drawing Sheets

OTHER PUBLICATIONS

Burchell et al, Development and Characterization of Breast Cancer Reactive Monoclonal Antibodies Directed to the Core Protein of the Human Milk Mucin, Cancer Research, vol. 47, pp. 5476–5482, Oct. 15, 1987.

Jerome et al, Cytotoxic T–Lymphocytes Derived from Patients with Breast Adenocarcinoma Recognize an Epitope Present on the Protein Core of a Mucin Molecule Preferentially Expressed by Malignant Cells, Cancer Res., vol. 51, pp. 2908–2916, 1991.

Bernstein et al, A General Synthesis of Model Glycoproteins: Coupling of Alkenyl Glycosides to Proteins, Using Reductive Ozonolysis Followed by Reductive Amination with Sodium Cyanoborohydride, Carbohydrate Research, vol. 78, pp. C1–C3, 1980.

Iijima et al, Total Synthesis of 3–O–[2–Acetamido–6–O–(N–Acetyl–a–D–Neuraminyl)–2–Deoxy–a–D–Galacto syl]–L–Serine and a Stereoisomer, Carbohydrate Research, vol. 172, pp. 183–193, 1988.

Kochetokov, Synthesis of Fragments of Bacterial Polysaccharides and their Application for the Preparation of Synthetic Antigens, Pure & Appl. Chem., vol. 56, No. 7, pp. 923–938, 1984.

James et al, The Action of Alkaline Reagents on 2:3–1:6– and 3:4–1:6 Dianhydro 3–Talose. A Constitutional Synthesis of Chondrosamine and Other Amino–Sugar Derivatives, J. Chem. Soc., pp. 625–628, 1946.

Gray et al, The Direct Coupling of Oligosaccharides to Proteins and Derivatized Gels, Archives of Biochemistry and Biophysics, vol. 163, pp. 426–428, 1974.

Hakomori, Aberrant Glycosylation in Tumors and Tumor–Associated Carbohydrate Antigens, Advances in Cancer Research, vol. 52, pp. 257–331, 1989.

Samuel et al, Human Tumor Associated TF Antigen, Cancer Research, vol. 50, pp. 4801–4808, 1991.

Itzkowitz et al, A Novel Mucin Antigen Associated with Prognosis in Colorectal Cancer Patients, Cancer, vol. 66, pp. 1960–1966, 1990.

Hanisch et al, A B72.3 Second–Generation–Monoclonal Antibody (CC49) Defines the Mucin–Carried Carbohydrate Epitope GalB(1–3)[NeuAca(2–6)]GalNAc, Biol. Chem. Hoppe–Seyler, vol. 370, pp. 21–26, 1989.

Yonezawa et al, Sialosyl–Tn Antigen, its Distribution Normal Human Tissues and Expression in Adenocarcinomas, Anatomic Pathology, vol. 98, pp. 167–174, 1992.

Orntoft et al, O–Linked Mucin–Type Glycoproteins in Normal and Malignant Colon Mucosa: Lack of T–Antigen Expression and Accumulation of Tn and Sialosys–Tn Antigens in Carcinomas, Int. J. Cancer, vol. 45, 666–672, 1990.

Diakur et al., Synthesis of GD3 as a 4–Methyl–3–Pentenyl Glycoside and Subsequent Conjugation to HSA, J. Carbohydrate Chemistry, vol. 13(5), pp. 777–797, 1994.

M.A. Bernstein et al., Synthesis of Model Glycoproteins: Coupling of Alkenyl Glycosides to Proteins, Using Reductive Ozonolysis Followed By Reductive Amination With Sodium Cyanoborohydride, Carbohydrate Research, vol. 78, C1–C3, 1980.

R. T. Lee et al., Synthesis of 3–(2–Aminoethylthio)Propyl Glycosides, Carbohydrate Research, vol. 37, No. 1, pp. 193–201, 1974.

S. Hanessian et al., Conformational Analysis of the Carbohydrate Portion of T and Tn Haptens By NMR Spectroscopy and Molecular Modeling, Tetrahedron, vol. 50, No. 1, pp. 77–92, 1994.

D. Cabaret et al., Amphiphilic Liposaccarides. Synthesis and Reductive Cleavage of C–Allyl, O–Allyl, and O–Butenyl Clycosyl Derivatives, Carbohydrate Research, vol. 189, pp. 341–348, 1989.

G.O. Aspinall et al., Synthesis of Allyl Glycosides for Conversion Into Neoglycoproteins Bearing Epitopes of Mycobacterial Glycolipid Antigens, Carbohydrate Research, vol.216, pp. 337–355, 1991.

G.O. Aspinall et al., A Stereoselective Synthesis of Pyruvic 4, 6–Acetals of D–hexopyranose Residues, Carbohydrate Research, vol. 200, pp. 247–256, 1990.

K.R. Holme et al., Preparation and Characterization of N–(2–Glycosyloxy)Ethyl)Chitosan Derivatives, Carbohydrate Research, vol. 225, pp. 291–306, 1992.

E. Müller, Methoden der Organischen Chemie, Houben–Weyl, Band VII, Teil 1, pp. 333–334, 1954.

T.C. Wong et al., Synthesis of D–Galactosamine Derivatives and Binding Studies Using Isolated Rat Hepatocytes, Carbohydrate Research, vol. 170, pp. 27–46, 1987.

R.W.Jeanloz et al., The Synthesis of Allyl 2–Acetamido–3, 6–DI–O–Benzyl–2–deoxy–Alpha–D–Glucopyranoside and of Chitobiose Derivatives By The Oxazoline Procedure, Carbohydrate Research, vol. 53, pp. 67–84, 1977.

R. Gigg et al., Synthesis of Propyl 4–O–(3,6,Dl–O–Metjyl–Beta–D–Gluco–Pyranosyl)–2,3–DI–O–Methyl–Alpha–D–Rhamno–Pyranoside, Carbohydrate Research, vol. 141, pp. 91–97, 1985.

H.A. El–Shenawy et al., Studies of the Synthesis of Propyl 4O–Beta–D–Galactopyranosyl–Alpha–D– Galactopyranoside, Carbohydrate Research, vol. 131, pp. 227–238, 1984.

FIG. 4
FISHER GLYCOSIDATION
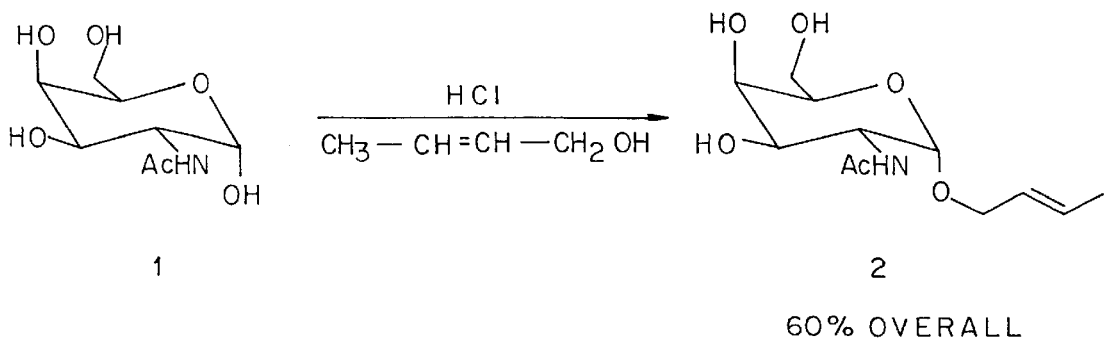
60% OVERALL
SYNTHESIS VIA 2-AZIDOGALACTOSE
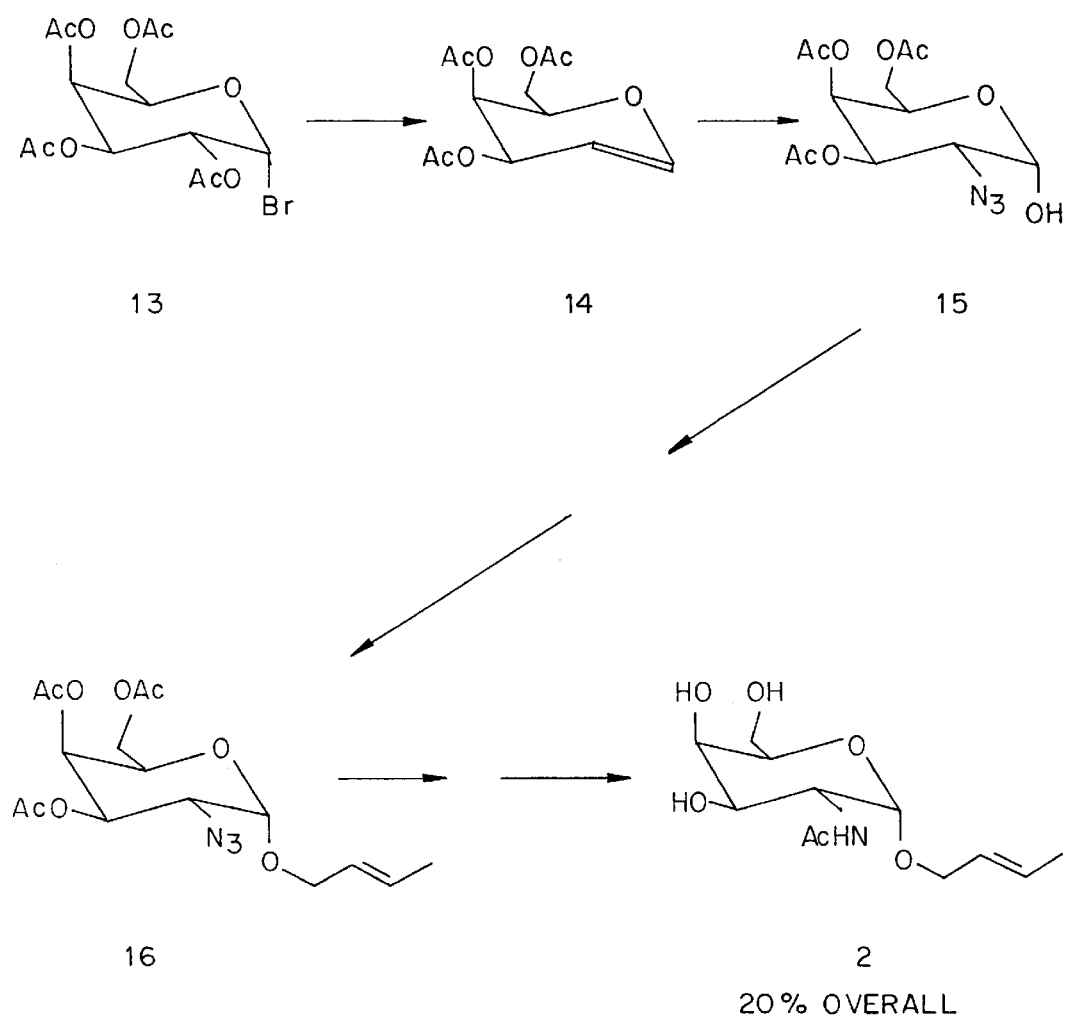
20% OVERALL

FIG. 6
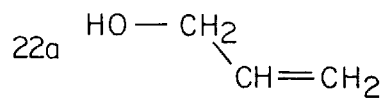
22a
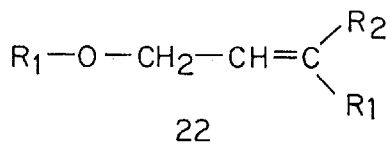
22
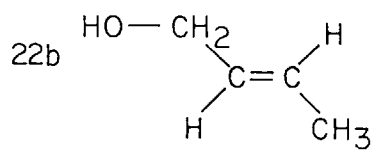
22b
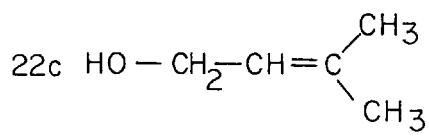
22c
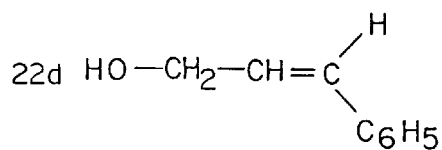
22d
22e  HO—$CH_2$—$CH_2$—O—$CH_2$—CH=$CH_2$
22f  HO—$CH_2$—$CH_2$—O—$CH_2$—CH=CH—$CH_3$
22g  HO—$CH_2$—$CH_2$—$CH_2$—$CH_2$—$CH_2$—O—$CH_2$—CH=$CH_2$
22h  HO—$CH_2$—$CH_2$—$CH_2$—$CH_2$—$CH_2$—O—$CH_2$—CH=CH—$CH_3$ FIG. 7
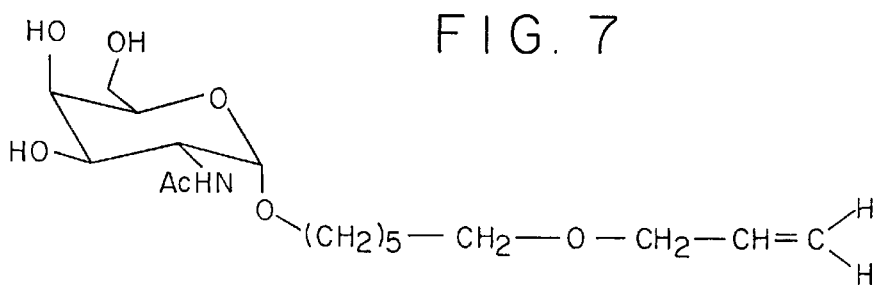
23
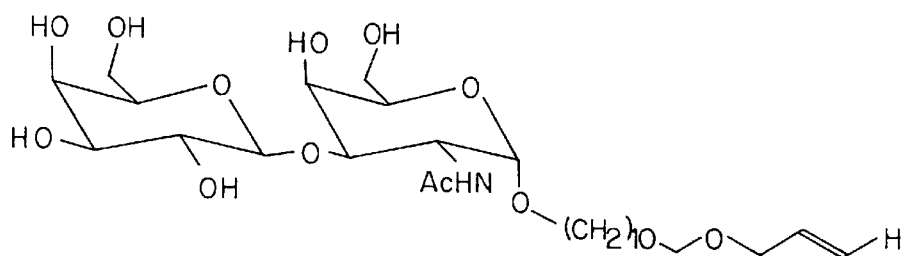
24
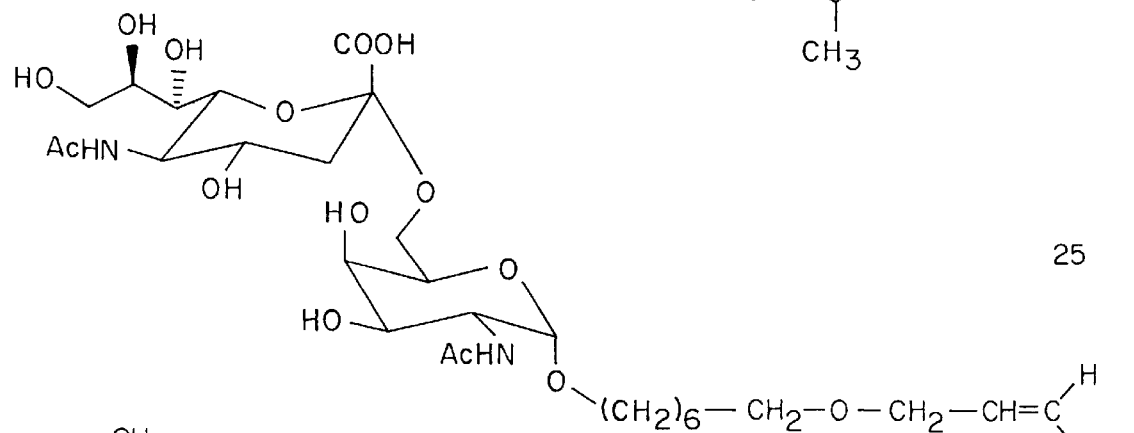
25
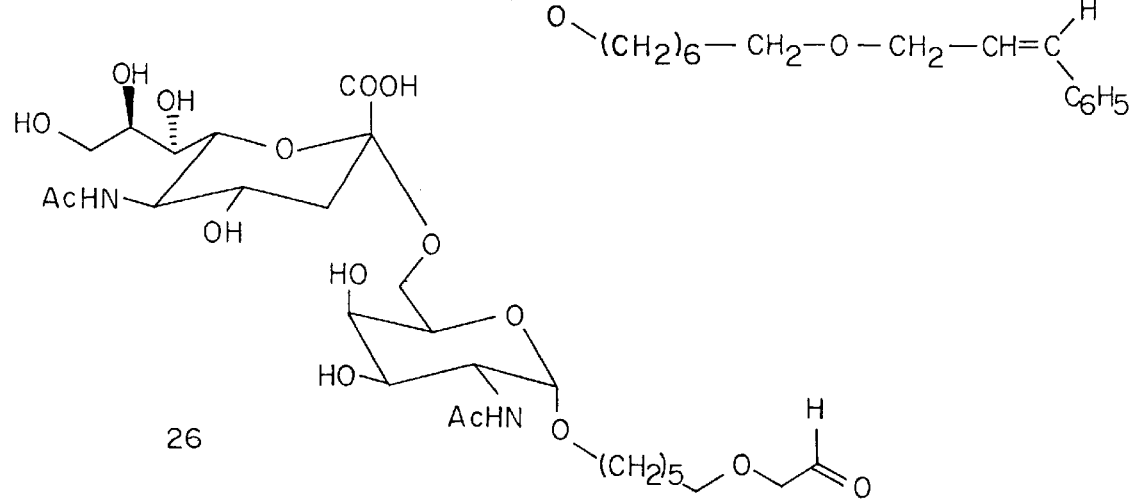
26
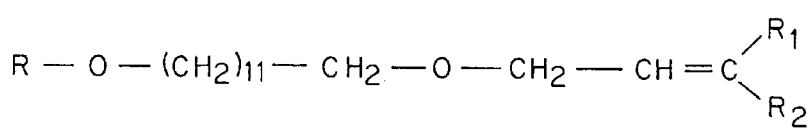
27

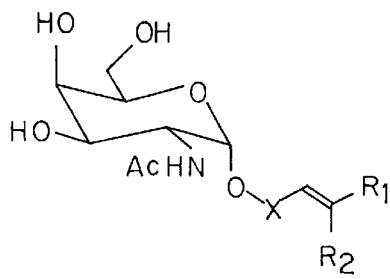
28
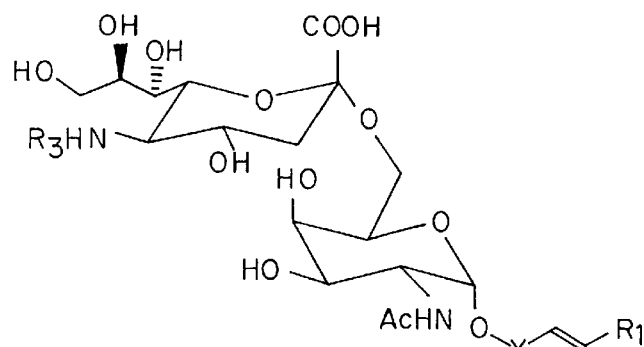
29a R₃ = CH₃CO (ACETYL)
29b R₃ = HOCH₂CO (GLYCOLYL)
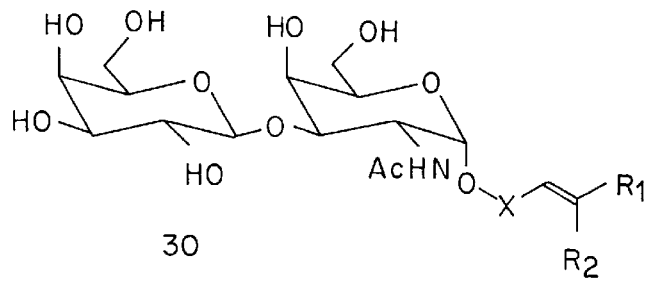
30
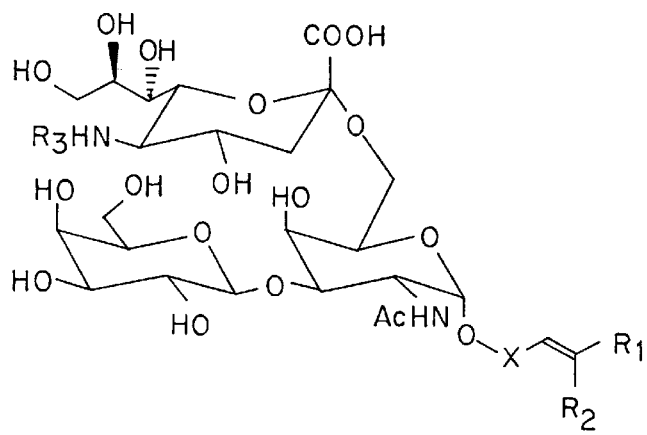
31a R₃ = CH₃CO (ACETYL)
31b R₃ = HOCH₂CO (GLYCOLYL)
FIG. 8

PROCESS FOR PREPARATION OF GLYCOSIDES OF TUMOR-ASSOCIATED CARBOHYDRATE ANTIGENS

This application is a continuation of application Ser. No. 08/235,954, filed May 2, 1994, now abandoned.

BACKGROUND OF THE INVENTION

1. Field of the Invention

The present invention relates to the preparation of novel glycosides of tumor-associated carbohydrate haptens.

2. Description of the Background Art

Tumor Associated Carbohydrate Antigenic Determinants. Numerous antigens of clinical significance bear carbohydrate determinants. One group of such antigens comprises the tumor-associated mucins (Roussel, et al., *Biochimie* 70, 1471, 1988).

Generally, mucins are glycoproteins found in saliva, gastric juices, etc., that form viscous solutions and act as lubricants or protectants on external and internal surfaces of the body. Mucins are typically of high molecular weight (often>1,000,000 Dalton) and extensively glycosylated. The glycan chains of mucins are O-linked (to serine or threonine residues) and may amount to more than 80% of the molecular mass of the glycoprotein. Mucins are produced by ductal epithelial cells and by tumors of the same origin, and may be secreted, or cell-bound as integral membrane proteins (Burchell, et al., *Cancer Res.*, 47, 5476, 1987; Jerome, et al., *Cancer Res.*, 51, 2908, 1991).

Cancerous tissues produce aberrant mucins which are known to be relatively less glycosylated than their normal counter parts (Hull, et al., *Cancer Commun.*, 1, 261, 1989). Due to functional alterations of the protein glycosylation machinery in cancer cells, tumor-associated mucins typically contain short, incomplete glycans. Thus, while the normal mucin associated with human milk fat globules consists primarily of the tetrasaccharide glycan, gal β1–4 glcNAcp1–6(gal β1–3) gal NAc-α and its sialylated analogs (Hull, et al.), the tumor-associated Tn hapten consists only of the monosaccharide residue, α-2-acetamido-3-deoxy-D-galactopyranosyl, and the T-hapten of the disaccharide β-D-galactopyranosyl-(1–3)α-acetamido-2-deoxy-D-galactopyranosyl. Other haptens of tumor-associated mucins, such as the sialyl-Tn and the sialyl-(2–6)T haptens, arise from the attachment of terminal sialyl residues to the short Tn and T glycans (Hanisch, et al., *Biol. Chem. Hoppe-Seyler*, 370, 21, 1989; Hakormori, *Adv. Cancer Res.*, 52:257, 1989; Torben, et al., *Int. J. Cancer*, 45 666, 1980; Samuel, et al., *Cancer Res.*, 50, 4801, 1990).

The T and Tn antigens (Springer, *Science*, 224, 1198, 1984) are found in immunoreactive form on the external surface membranes of most primary carcinoma cells and their metastases (>90% of all human carcinomas). As cancer markers, T and Tn permit early immunohistochemical detection and prognostication of the invasiveness of some carcinomas (Springer). Recently, the presence of the sialyl-Tn hapten on tumor tissue has been identified as an unfavorable prognostic parameter (Itzkowitz, et al. *Cancer*, 66, 1960, 1990; Yonezawa, et al., *Am. J. Clin. Pathol.*, 98 167, 1992). Three different types of tumor-associated carbohydrate antigens are highly expressed in common human cancers. The T and Tn haptens are included in the lacto series type, and type 2 chains. Additionally, cancer-associated ganglio chains and glycosphingolipids are expressed on a variety of human cancers.

The altered glycan determinants displayed by the cancer associated mucins are recognized as non-self or foreign by the patient's immune system (Springer). Indeed, in most patients, a strong autoimmune response to the T hapten is observed. These responses can readily be measured, and they permit the detection of carcinomas with greater sensitivity and specificity, earlier than has previously been possible. Finally, the extent of expression of T and Tn often correlates with the degree of differentiation of carcinomas. (Springer).

Carbohydrate-Protein Conjugates. Because the tumor-associated antigens are useful in diagnosis and monitoring of many types of carcinomas, and may also be useful in treatment, many workers have synthesized glycosides of the carbohydrate haptens and of their sialylated analogs and have used these glycosides to conjugate the haptens to proteins or synthetic peptide carriers. The glycosides have generally included an aglycon moiety from which a highly reactive functionality can be generated without altering the saccharide portion of the respective hapten glycoside. The "activated" hapten glycosides are then reacted with amino groups of the proteins or synthetic peptide carriers to form amide of Schiff base linkages. The Schiff base grouping can be stabilized by reduction with a borohydride to form secondary amine linkages; the whole coupling process is then referred to as reductive amination. (Gray, *Arch. Biochem. Biophys.*, 163, 426, 1974).

Lemieux et al. disclosed artificial antigens in which a T-antigenic determinant is coupled to a protein or polysaccharide carrier by means of an α-O-glycosidically linked —O—$(CH_2)_n$COR linking arm (U.S. Pat. Nos. 4,794,176; 4,866,045; 4,308,376; 4,362,720; 4,195,174; Can. J. Chem., 57, 1244, 1979). In this process, a D-galactal derivative is converted by azidonitration into a 2-azido-2-deoxy-D-galactopyransoyl nitrate which reacts with quaternary ammonium halides to form a 2-azido-2-deoxy-D-galactopoyranosyl halide. This halide is used as a glycosyl donor to form an α-glycoside with the alcohol, 9-hydroxynonanoic acid ethyl (or methyl) ester (Lemieux, et al., U.S. Pat. No. 4,137,401). In subsequent steps, the 2-azido-2-deoxy-D-galactopyranosyl unit is converted into the 2-acetamido-deoxy-D-galactopyranosyl unit. This can be suitably protected to attach additional glycosyl residues, such as the β-D-galactopyranosyl residue at 0–3 to form the T-hapten. Alternatively, the 2-acetamido-2-deoxy-α-D-galactopyranosyl glycoside may also be used directly as the Tn hapten.

To "activate" the linker arm, the 9-glycosyloxy fatty acid ester is converted into a 9-glycosyloxy fatty acid hydrazide. The hydrazide is oxidized to the 9-glycosyloxy-nonanoic acid azide which reacts, much like an acid halide, with amino groups of proteins or synthetic peptide carriers, to bind the hapten glycoside in an amide linkage.

The Lemieux process requires a 2-azido-2-deoxygalactosyl intermediate to enable the formation of the desired α-glycoside. Also, the ester group on the linking arm is frequently unstable during chemical manipulation required for the attachment of additional glycosyl residues to the 2-acetamido-2-deoxy-D-galactopyranosyl glycoside. Due to the multi-step nature of the process, over-all yields are low, and particularly the final coupling step of acyl azide to the protein or synthetic peptide carried can be inefficient, resulting in wastage of these extremely expensive hapten glycosides.

The 2-azido-2-deoxy-D-galactopyranosyl halide intermediate required for the preparation of the T and Tn haptens according to the process of Lemieux may be directly prepared by azidochlorination of a D-galactal derivative (Naicker, et al., U.S. Pat. No. 4,935,503). Another route to 2-azido-2-deoxy-D-galactopyranosyl halides has been described by Paulsen, et al., *Chem. Ber.*, 111, 2358, 1978). The reaction of 1,6;2,3-dianhydro-D-talopyranose (James, *J. Chem. Soc.*, 625, 1946) with sodium azide affords a derivative of 2-azido-2-deoxy-D-galacto-pyranose which may be further converted into a glycosyl halide donor suitable for glycosylation of the Lemieux linker arm 9-hydroxynonanoic acid methyl (or ethyl) ester or an equivalent linker moiety.

Several other linking arms for conjugating haptens to proteins or synthetic peptide carriers are known to the art (Kolar, U.S. Pat. No. 4,442,284, amino acid; Feizi, U.S. Pat. No. 4,563,445, alkyl, hydroxyl alkyl, alkenyl or ether linker; Koganty, U.S. Pat. No. 5,055,562, a covalent linker comprising at least one fluorocarbon chain).

Jennings et al., U.S. Pat. No. 4,356,170, derive their carbohydrate haptens from naturally-occurring bacterial polysaccharides. Activation of the hapten is effected by controlled periodate oxidation of vicinal hydroxyl groups to form aldehyde functions. The reductive amination procedure is used to conjugate the haptens to the proteins or synthetic peptide carriers. The process of Jennings, et al., is unsuitable for preparing conjugates of the T and Tn haptens because the haptens are not readily available in pure form from natural sources, and periodate oxidation would presumably destroy the T and Tn epitopes.

Roy, et al., in U.S. Pat. No. 5,034,516, have disclosed conjugates containing carbohydrate haptens, prepared by synthesis of allyl glycosides which were subsequently co-polymerized with suitable co-monomers such as acrylamide (Kochetkov, *Pure and Appl. Chem.*, 56, 923, 1984). However, the resulting co-polymeric conjugates are often poorly immunogenic, and the method of Roy, et al., does not permit the attachment of the haptens to the desired protein or synthetic peptide carriers.

Bernstein, et al. (*Carbohydr. Res.*, 78, C1–C3, 1980) disclosed ozonolytic cleavage of allyl glycosides of carbohydrate haptens to produce aldehyde glycoside derivatives which may be coupled to proteins or peptide carriers by reductive amination. However, ozonolytic cleavage of allyl glycosides results in the formation of formaldehyde as a by-product of the desired hapten glycoside aldehyde derivatives. Formaldehyde contributes to denaturation of the protein carriers and competes with the hapten glycoside aldehyde derivatives for available amino groups of the proteins or peptide carriers. Unfortunately, because formaldehyde is strongly hydrated and water soluble, there is no simple means of removing formaldehyde from the solutions containing the hapten glycoside aldehyde derivatives.

Several groups of investigators have reported methods for preparation of the sialyl (2–6)T and sialyl-Tn antigens. Paulsen, et al., *Carbohydr. Res.*, 137, 63, 1985) describe the synthesis of the disaccharide α-sialyl-(2–6)-β-2-acetamide-2-deoxy-D-galactopyranose. Lijima, et al. *Carbohydr. Res.*, 172, 183, 988) disclosed the synthesis of the sialyl-Tn hapten as a glycoside of L-serine, using as an intermediate a protected allyl glycoside of sialyl-(2–6)-2-azido-2-deoxy-D-galactopyranose.

Conjugation of sialic acid-containing oligosaccharide haptens to carriers by the Lemieux process is highly impractical due to the difficulty in distinguishing the carboxylic ester functions on sialic acid and on the linker arm.

Thus, the process taught by prior workers for preparing glycoconjugate antigens comprising the Tn, T, sialyl-Tn, and sialyl-(2→6)T haptens involve expensive starting materials such as D-galactal derivatives or 1,6,2,3-dianhydro-D-talose which are processed to the desired glycoconjugates in multistep reaction sequences with low over-all yields. Use of these processes for preparing the required glycoconjugates in commercial quantities of pharmaceutical grade purity is not practical. There is therefore a need for a process that provides these important glycoconjugates in relatively large quantities and at reasonable cost.

Glycosoylation Methods

The chemical synthesis of oligosaccharide, especially in a stereochemically controlled manner, can be challenging. The classical Koenigs-Knorr method, developed in 1901, involves glycosylating a sugar (the glycosyl acceptor) with a glycosyl bromide or chloride, using a heavy metal salt catalyst. A large number of alternatives are discussed by Schmidt, Angew. Chem. Int. Ed. Engl. 25:212–35 (1988) who in passing discusses Fischer-type glycosylations, which are acid catalyzed. He comments that this method "does not involve an isolable intermediate and, partly as a result of its reversibility has attained hardly any significance for the synthesis of complex saccharides". Thus, Schmidt considers and rejects the Fischer approach.

Schmidt observes that 2-amino sugars, especially N-acetylglucosamine and N-acetylgalactosamine, are of great importance in biologically occurring complex oligosaccharides and glycoconjugates. He advocates glycosidic coupling of GlcNAc via the trichloroacetimidate method, with various catalysts. A person of ordinary skill in the art would reasonably infer that this is Schmidt's preferred approach to GalNAc coupling, too.

Flowers, Meth. Enzymol., 138:359 (1987) also alludes (pp. 373–3) to the Fischer-type glycosylation. While he indicates that "the preferred stability of α-D-glycopyranosides in most cases enables their isolation in reasonable yield," he cautions that "this approach is usually not feasible for glycosides of disaccharides, since alcoholysis of the interglycosidic linkage competes with glycosylation of the reducing OH." He concludes that "complex mixtures often result" from Fischer-type glycosylation.

SUMMARY OF THE INVENTION

The present invention provides a method for the formation of conjugates of a carbohydrate hapten, through a linking arm, with a protein or other aminated compounds.

Carbohydrates are a class of molecules that are hard to synthesize in any quantity. Significantly, the carbohydrate structures that are tumor-associated are not readily available from natural sources. These structures normally must be produced only by chemical or enzymatic synthesis. Though the monosaccharide raw materials have become available in large quantities during the past several years, their manipulations for synthesis is rather cumbersome. A particularly tough molecule to handle is the N-acetyl D-galactosamine 1 which is an important O-linked glycoside that is nearly exclusively α-linked to serine and threonine in glycoproteins and mucins that are characterized by the presence of O-linked glycosides. Its α-linkage to serine and threonine is a unique biosynthetic step that is followed by the extension of the structure to complex polylactosamine biosynthesis and termination process that give the unique characteristics to the glycoproteins called mucins. The interruption of this carbohydrate biosynthesis following the formation of α-galactosaminides, is widely regarded as tumor associated. Consequently, N-acetylgalactosamine, also known as Tn antigen, and its aberrantly glycosylated structures such as TF, STN and STF are tumor associated.

During the early 1980s N-acetylgalactosamine was available only in limited quantities. The difficulty of its chemical manipulation and scarcity led to the development of 2-azidogalactose 15 (FIG. 4) as a precursor for N-acetylgalactosamine. The presence of N-acetyl group at 2-position of the pyranose ring makes it impossible to prevent its ready participation in any glycosidic bond formation resulting in the undesirable oxazoline 18 (Eq. 1, FIG. 5).

In 2-azidogalactose, the azido group is a non-participating group and hence the reaction proceeds without its interference. But in spite of this facility, the elaborate synthetic process leading to the 2-azidogalactose adds significant amount of time and cost to the final glycoside.

Although Fischer glycosidation involves the acid catalyzed formation of α-linkage between carbohydrate and an aglycon, the reaction suffers from complexity and numerous undesired side products. In spite of its discovery several decades ago, it has not been utilized as a significant synthetic route for this reason. We have reinvestigated the Fischer glycosidation and discovered that it has a previously unrecognized value in the synthesis of tumor associated carbohydrate antigens along with processes like ozonolysis and reductive amination using olefinic linker arms.

Thus, in one aspect of the invention, alpha olefinic glycoside is prepared by a Fisher-type glycosylation of an olefinic alcohol. The resulting alpha olefinic glycoside is then ozonolyzed as shown below:

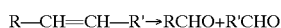

R—CH=CH—R'→RCHO+R'CHO where R is the hapten and R' is substituted or unsubstituted alkyl, aryl or arylalkyl. The hapten aldehyde is then reacted with the amino function of the partner molecule:

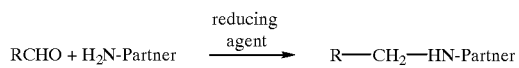

$$RCHO + H_2N\text{-Partner} \xrightarrow{\text{reducing agent}} R\text{—}CH_2\text{—}HN\text{-Partner}$$

In a second aspect of the invention, the olefinic glycoside may be either an alpha glycoside (preferably obtained as set forth above) or a beta glycoside (as further discussed below) obtained in either case by glycosylation of an unsaturated alcohol. However, the olefinic glycoside is chosen so that the second carbonyl will not be formaldehyde. The byproduct formed during ozonolysis of the glycosides of the present invention is a higher carbonyl compound, i.e., aldehyde such as acetaldehyde or propionaldehyde, or a ketone, which can be removed easily by entrainment with an inert gas prior to the coupling step. These carbonyl compounds, which are dehydrated to a lesser extent than formaldehyde, do not compete with the glycosyl aldehyde derivative for available amino groups on the carrier protein, nor do these higher carbonyl compounds denature the proteins. Thus, problems of protein denaturation or competing reactivity of formaldehyde are avoided.

BRIEF DESCRIPTION OF THE DRAWING

FIG. 4: Comparison of TN synthesis through Fisher glycosidation and through the use of intermediate 2-Azidogalactose as precursor. In the figure, n is a controllable number with a fair degree of accuracy but always limited by the number of available amino functions on the carrier molecule.

FIG. 6: Shows a general formula of the olefinic alcohol 22 and examples of alcohols based on the general formula (22a–h) for use in synthesis of linker arms of various configurations. In the figures, $R_1$=H or R—O—$(CH_2)_{2-10}$— and $R_2$ and $R_3$ may be H, alkyl, aryl, etc.

FIG. 7: Shows haptens with linker arms of various lengths and configurations (23, 24, 25) and with a reactive 2-oxo-aldehyde 26. In the figure, R=α and β linked carbohydrate structure, n=1 to 10, and $R_1$ and $R_2$=any combination of H, alkyl, aryl or arylalkyl.

FIG. 8: Shows the acetyl and glycolyl analogues of T series of haptens with a general linker arm. In the figure, X=—$CH_2$— or —$(CH_3)_{2-10}$—O—, and $R_2$ and $R_3$ are chosen from: H, $DH_3$, $C_2H_5$, $C_6H_5$, —$CH_2C_6H_5$, etc.

DETAILED DESCRIPTION OF THE PREFERRED EMBODIMENTS OF THE INVENTION

Figure 1:
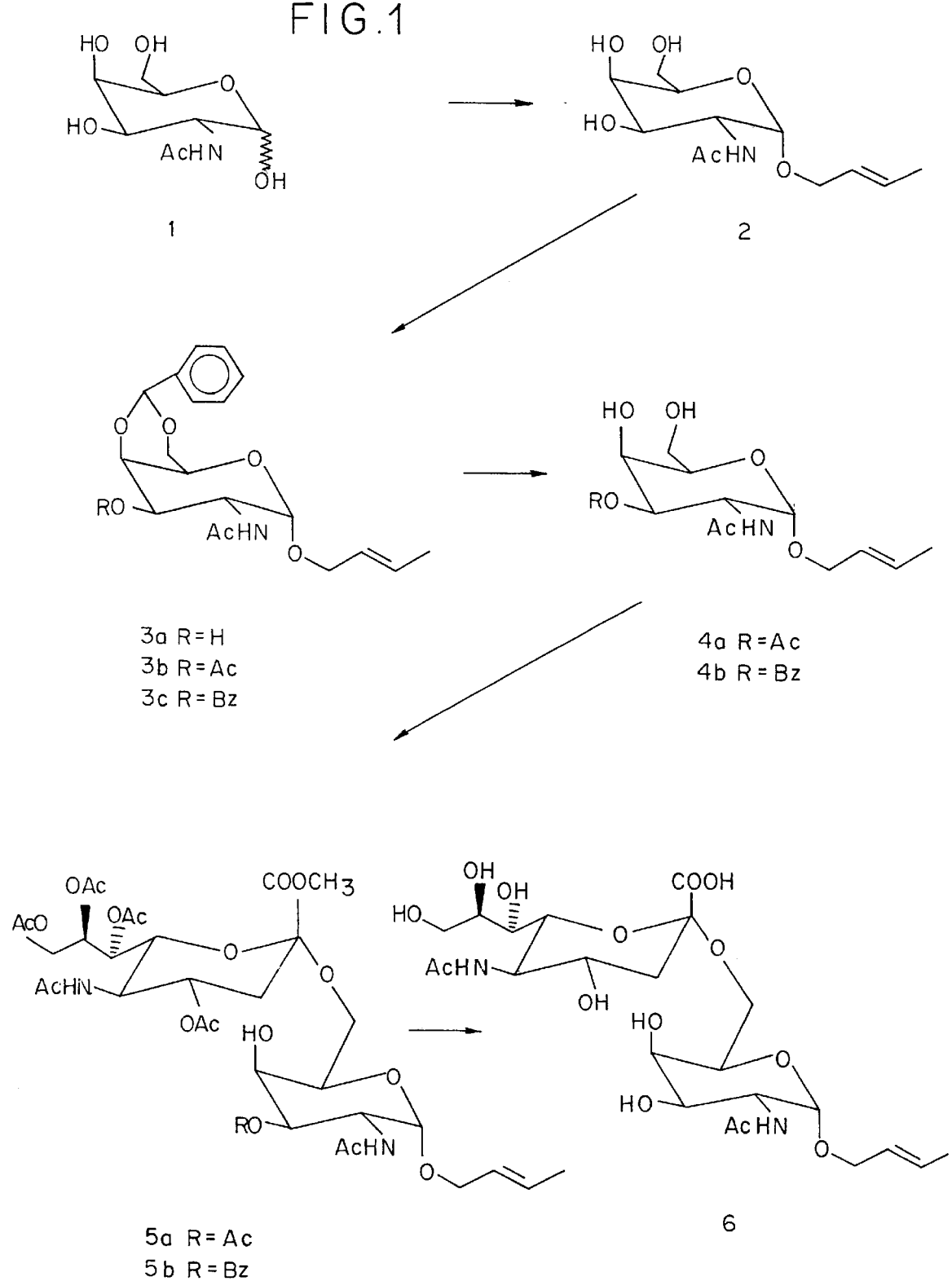
FIG. 1: Shows the synthetic scheme for TN and STN haptens.
Figure 2:
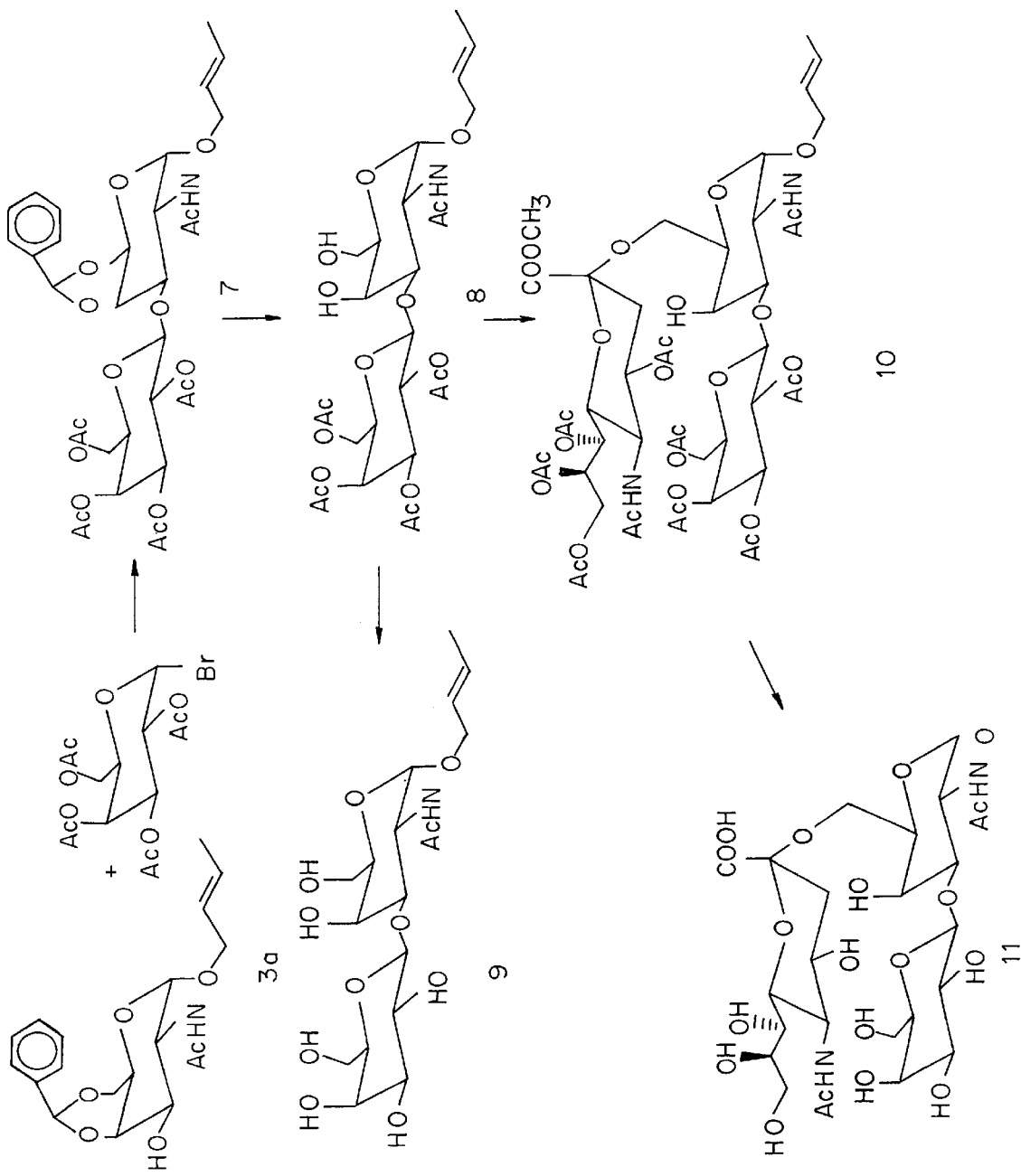
FIG. 2: Shows the synthetic scheme for TF and STF haptens.
Figure 3:
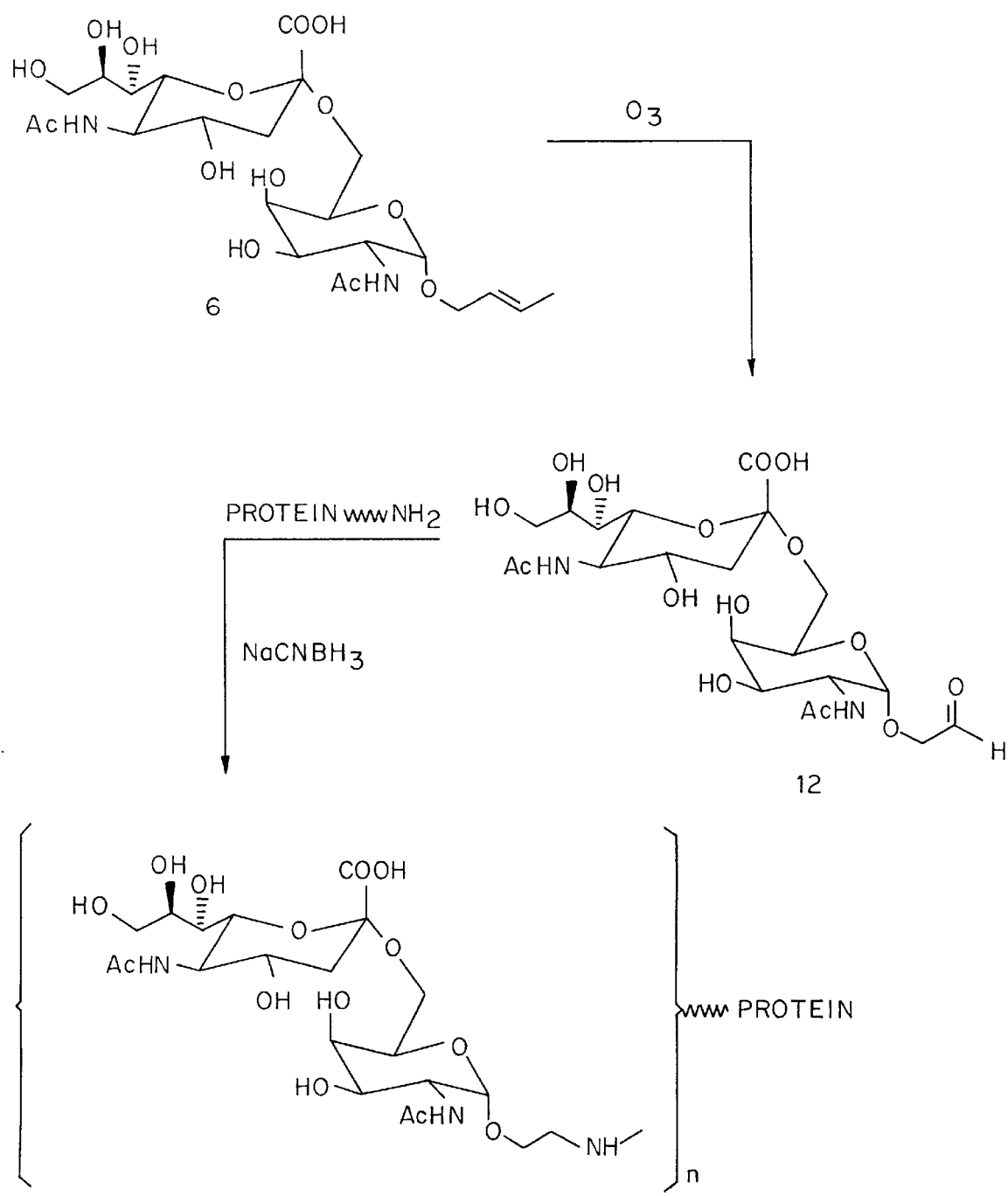
FIG. 3: Shows ozonolysis to generate aldehyde and conjugation to protein through reductive amination.
Figure 5:
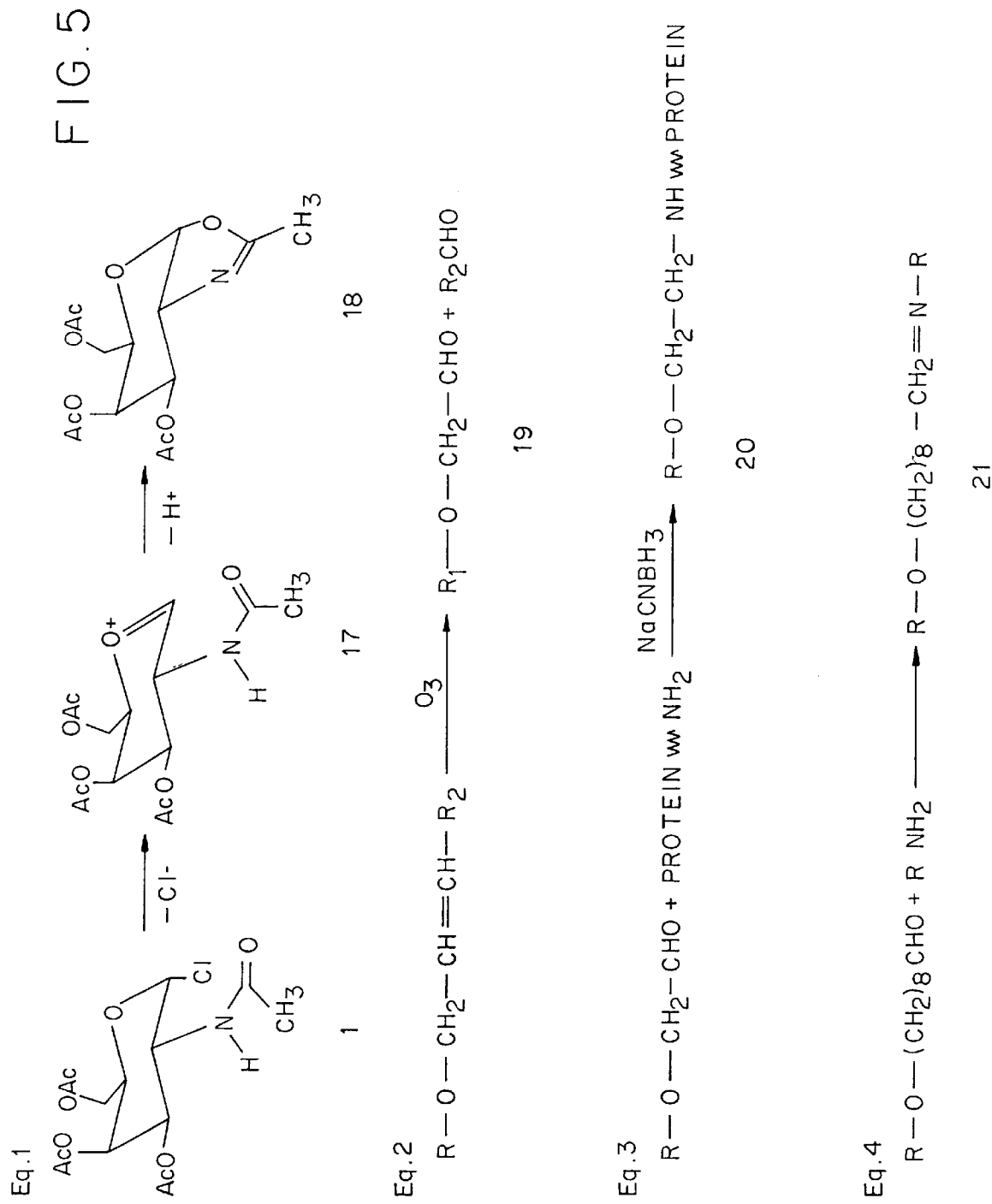
FIG. 5: Shows chemical equations for the formation of oxazoline (EQ.1), ozonolysis (EQ.2), reductive amination (EQ.3) and Schiff's base formulation (EQ.4).

In the present invention, a conjugate is formed which comprises a carbohydrate hapten, a linking arm, and a conjugation partner. The conjugate is obtained by glycosylating an unsaturated alcohol, ozonolyzing the olefinic glycoside, and reacting the resulting carbonyl glycoside with an amino function of the conjugation partner.

Carbohydrate Haptens

A variety of carbohydrates can be conjugated according to the present invention, for use particularly in detecting and treating tumors. The Tn, T, sialyl Tn and sialyl (2→6)T haptens are particularly preferred.

In particular, for detecting and treating tumors, the three types of tumor-associated carbohydrate epitopes which are highly expressed in common human cancers are conjugated to aminated compounds. These particularly include the lacto series type 1 and type 2 chain, cancer associated ganglio chains, and neutral glycosphingolipids.

Examples of the lacto series Type 1 and Type 2 chains are as follows:

Tn: GalNAcα1→

Sialosyl-Tn: NeuAcα→6GalNAcα1→

Sialosyl-T: NeuAcα→6(Galβ1→3)GalNAcα1→

```
NeuAcα→6GalNAcα1→
              3
              ↓
            Galβ 1
```

T: Galβ1→3GalNAcα1→

Examples of cancer-associated ganglio chains that can be conjugated to aminated compounds according to the present invention are as follows:

CANCER ASSOCIATED GANGLIO CHAINS

GM3: NeuAcα2→3Galβ1→4Glcβ1→

GD3: NeuAcα2→8NeuAcα2→3Galβ1→4Glcβ1→

GM2:  GalNAcβ1→4Galβ1→4Glcβ1→
                3
                ↑
            NeuAcα 2

GM4: NeuAcα2→3Galβ1→

GD2:   GalNAcβ1→4Galβ1→4Glcβ1→
                    3
                    ↑
         NeuAcα2→8NeuAcα 2

GM1:  Galβ1→3GalNAcβ1→4Galβ1→4Glcβ1→
                        3
                        ↑
                    NeuAcα 2

GD-1a: NeuAcα2→3Galβ1→3GalNAcβ1→4Galβ1→4Glcβ1→
                                3
                                ↑
                            NeuAcα 2

GD-1b:   Galβ1→3GalNAcβ1→4Galβ1→4Glcβ1→
                                3
                                ↑
                 NeuAcα2→8NeuAcα 2

In addition to the above, neutral glycosphingolipids can also be conjugated to aminated compounds according to the present invention:

SELECTED NEUTRAL GLYCOSPHINGOLIPIDS

Globotriose: Galα→4Galβ1→4Glcβ1→
Globotetraose: GalNAcβ1→3Galα→4Galβ1→4Glcβ1→
Globopentaose:
 GalNAcα1→3GalNAcβ1→3Galα→4Galβ1→4Glcβ1→
Isoglobotriose: Galα→3Galβ1→4Glcβ1→
Isoglobotetraose:
 GalNAcβ1→3Galα1→3Galβ1→4Glcβ1→
Mucotriose: Galβ1→4Galβ1→4Glcβ1→
Mucotetraose: Galβ1→3Galβ1→4Galβ1→4Glcβ1→
Lactotriose: GalNAcβ1→3Galβ1→4Glcβ1→
Lactotetraose:
 GalNAcβ1→3GalNAcβ1→3Galβ1→4Glcβ1→
Neolactotetraose:
 Galβ1→4GlcNAcβ1→3Galβ1→4Glcβ1→
Gangliotriose: GalNAcβ1→4Galβ1→4Glcβ1→
Gangliotetraose: Galβ1→GlcNAcβ1→4Galβ1→4Glcβ1→
Galabiose: Galα→4Galβ1→
9-O-Acetyl-GD3: 9-O-Ac-NeuAcα2→8NeuAcα2→3Galβ1→4Glcβ1→

Synthesis of the Hapten

The hapten may be synthesized by carbohydrate synthesis techniques appropriate to the carbohydrate structure in question. In one embodiment, the entire hapten is synthesized, and then one end is linked to the linking arm. In a second embodiment, the proximal end sugar is conjugated to the linking arm, and the remainder of the hapten is then built up. In a third embodiment, the proximal sugar/linking arm conjugate is formed, and then itself linked to the partner molecules. The hapten is then built up on the sugar of this tripartite conjugate. Other variations are possible. The second embodiment mentioned above is preferred.

The Linking Arm

The linking arm is an olefin derived from one of the unsaturated alcohols described in a later section, preferably a crotyl alcohol.

Synthesis of the Sugar-Linker Arm Intermediate (the Glycoside)

When the sugar is to be alpha-glycosidically linked to the olefinic linking arm, a Fisher-type glycosylation is preferred. In a Fisher-type glycosylation, an acid is used to catalyze the reaction of a reducing sugar with an excess of an alcohol, as described by Fischer, Chem. Ber., 26: 2400 (1983). The acid may be any acid capable of performing this function. Such acids may be dry inorganic acids such as $BF_3$, HCl, HBr, HI, $HNO_3$, and $H_3PO_4$, or organic acids, whether aliphatic or aromatic. Para-toluene sulfonic acid and HCl are preferred.

Among most O-linked glycoproteins, serine and threonine are the two hydroxyamino acids that almost exclusively carry the a-linked N-acetylgalactsamine as the primary hexose. N-acetylgalactosamine appears to be unique to serine and threonine as primary α-O-linked carbohydrate structure. While synthesizing the tumor associated carbohydrate antigens this linkage must be preserved. Fischer glycosidation imposes severe limitations on its general applicability because of the strongly acidic reaction medium. Under these conditions all hydroxy solvents become reactive to the carbohydrate, as aglycons. The poor solubility of N-acetylgalactosamine limits most other solvents. Even otherwise, the reaction becomes very complex due to the side reactions yielding undesirable products.

Fisher glycosidation can be useful if an equilibrium is achieved between the reactants and products at an optimum concentration of acid, the temperature and duration of the reaction. We chose olefinic alcohols which are stable at mild temperatures and acidic conditions, as solvent for the reaction so that the large excess of solvent-reactant can effectively establish the equilibrium while limiting the destructive influence of the acid to the minimum. Our experience showed that use of freshly distilled linker arm as solvent minimized the side products while increasing the yield of the desired a-glycoside to about 60% at an optimum acid concentration (See table). A variety of aglycons have been proposed and can be utilised for this purpose (FIG. 6). FIG. 4 compares the simplicity of Fisher synthesis with a process that employs 2-azidogalactose, for the synthesis of TN-crotyl hapten.

We have discovered that the acid concentration significantly affects the yield of the desired product. If it is too low, the progress of the reaction is unsatisfactory. If it is overly increased, yield drops again possibly because the glycosidic bonds are sensitive to strong acid concentrations. We have reacted 600 g N-acetylgalactosamine in 12 kg crotyl alcohol, and added HCl in different mole percent, as a 6M solution in tetrahydrofuran, with these results:

| MOLE % | YIELD |
|--------|-------|
| 1.5    | ~20%  |
| 3.1    | 45%   |
| 4.8    | 60%   |
| 6.0    | 35%   |

Note that yield was maximized with a concentration of 4.8 mole % HCl.

The choice of reducing sugar is dependent on the hapten in question. For Tn, sialosyl-Tn, Sialosyl-T and T, it would be N-acetyl galactosamine.

It is also possible, by use of appropriate reactants and catalysts, to form a beta-glycosidic linkage between the hapten and the linking arm. Typically, the hapten's irrelevant hydroxyl functions are protected with acetyl or benzoyl groups. A glycosyl halide (fluoride, chloride, bromide) is prepared, and reacted with an acceptor alcohol in the presence of a catalyst such as a silver or mercury salt. The alpha/beta ratio is affected by the nature of the donor saccharide (including the protecting group at carbon 2), the catalyst, etc. See generally Paulsen, Chem. Soc. Per. 13:15 (1984), Schmidt, Angew. Chem. Int'l. Ed. Engl. 25:212 (1986), Flowers, Meth. Enzymol. 138:359 (1987), Paulsen, Strategies in Oligosaccharide Synthesis 317–355 (IUPAC 1985).

Generally, the acid-catalyzed reaction of a reducing sugar with an excess of an alcohol, as described by Fischer, *Chem. Ber.*, 26 2400 (1983) gives a mixture of glycosides of the alcohol, the ratio of these glycosides being determined by the relative stabilities of the various glycosides at equilibrium.

The Alcohol

FIG. 1 illustrates synthesis of various haptens using crotyl alcohol as the unsaturated alcohol. Of course, any unsaturated alcohol can be used to form the hapten glycoside. However, if glycosylation is to occur by a Fischer-type reaction, one must avoid those alcohols containing a terminal double bond and those whose high molecular weight would make their use in the Fischer glycosylation impractical.

A terminal double bond is undesirable because of the byproducts of the subsequent ozonolysis of the glycoside. Of crucial importance is the nature of the second carbonyl product formed together with the hapten glycoside carbonyl derivative. As noted above, it is undesirable to yield formaldehyde as a product. When crotyl alcohol is used as the olefinic aglycon moiety according to the process of the invention, the second carbonyl formed is acetaldehyde, which may be removed by simple entrainment with an inert gas, leaving the essentially pure hapten glycoside aldehyde derivative for high-yield coupling to the protein or peptide carrier. The specific substitution pattern at the double bond of the olefinic aglycon moiety of the hapten glycosides of the invention may also be chosen so that the second carbonyl product formed upon ozonolysis is propionaldehyde, acetone, or the like, which are all easily entrained or, in the case of higher aldehydes or ketones, removed by solvent extraction. However, the commercial usefulness of other unsaturated alcohols as the olefinic aglycon moiety in the process of the invention is limited only by their availability in large quantities at low cost, by their ability to form α-glycosides of N-acetylgalactosamine in the Fischer glycosylation, and by the ease of their ozonolytic cleavage to form the required hapten glycoside aldehyde derivatives.

The preferred unsaturated alcohols for use in the process of the resent invention are of the formula:

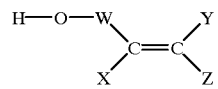

wherein W is $(CH_2)_n$ wherein n=1–20, and X, Y and Z are $(CH_2)_m H$, where m is 0–6; with the proviso that X, Y, and Z cannot all be H.

When m is 0, a hapten glycoside aldehyde forms on ozonolysis. Where m is 1 or more, then a hapten glycoside ketone forms on ozonolysis. Although the ketones can be used for conjugation according to the present invention, the aldehydes are more reactive and thus are the preferred compounds.

Where n is 1, X, Y, and Z preferably are not all H, as in that case the alcohol would have a terminal double bond.

Likewise, Y and Z preferably are not both H, as the alcohol would have a terminal double bond, and the ozonolysis would form formaldehyde, which is an undesired product of the reaction. Y and Z can be any combination of alkyl groups and alkyl groups or hydrogen, as long as the alkyl groups are not so bulky that they impede ozonolysis. The volatility of the aldehyde or ketone byproduct is not a limitation, because all higher aldehydes and ketones are immiscible with water, and can easily be removed by solvent extraction using a solvent such as chloroform, ether, dichloromethane, and the like. This is still a very simple physical separation, and does not adversely affect the hapten glycoside.

Specific examples of values for W, X, Y and Z are found in the following table:

| W      | X | Y        | Z        | Alcohol               | Ozonolysis          |
|--------|---|----------|----------|-----------------------|---------------------|
| —$CH_2$— | H | H        | H        | allyl alcohol         | formaldehyde        |
| —$CH_2$— | H | H        | $CH_3$   | crotyl alcohol        | acetaldehyde        |
| —$CH_2$— | H | $CH_3$   | H        | crotyl alcohol        | acetaldehyde        |
| —$CH_2$— | H | $CH_3$   | $CH_3$   | 3-methyl-but-2-en-1-ol | acetone            |
| —$CH_2$— | H | $CH_3$   | $CH_3CH_2$ | -3-methyl-pent-2-en-1-ol | methyl ethyl ketone |
| —$CH_2$— | H | $CH_3 CH_2$ | $CH_3$ | -3-methyl-pent-2-en-1-ol | methyl ethyl ketone |

-continued

| W | X | Y | Z | Alcohol | Ozonolysis |
|---|---|---|---|---------|------------|
| $-CH_2-$ | H | $CH_3 CH_2$ | $CH_3 CH_2$ | 3-ethyl-pent-2-en-1-ol | diethyl ketone |
| $-CH_2-$ | H | H | $CH_2 CH_3$ | -pent-2-en-1-ol | propionaldehyde |
| $-CH_2-$ | H | $CH_3 CH_2$ | H2 | -pent-2-en-1-ol | propionaldehyde |
| $-CH_2-$ | H | H | $CH_3CH_2CH_2$ | -hex-2-en-1-ol | n-butyraldehyde |
| $-CH_2-$ | H | $CH_3CH_2CH_2$ | H | -hex-2-en-1-ol | n-butyraldehyde |
| $-CH_2-$ | H | H | $CH_3$ $CH-$ $CH_3$ | -4-methyl-hex-2-en-1-ol-1 | isobutyraldehyde |
| $-CH_2-$ | H | H | $CH_3$ $CH-$ $CH_3$ | -4-methyl-hex-2-enol-1 | isobutyraldehyde |

Note that the first entry of the table above is not one of the preferred alcohols of the present invention, but is set forth for comparison purposes.

The use of an olefinic aglycon moiety with a specific substitution pattern at the double bond permits preparation of glycoconjugates of haptens with a high ratio of carbohydrate to protein. The conjugation of the T structure to human serum albumin using a ratio of 1.5:1 of carbohydrate hapten to protein (approximately a molar ratio of hapten to lysine of 4:1) yields about 20 haptens per mole of protein. The conjugation of sialyl Tn hapten to human serum albumin using 1.2:1 w/w of carbohydrate to protein (about a molar ratio of hapten to lysine of 2.4:1) yields 16 haptens per mole of protein.

Ozonolysis of the Glycoside

The olefinic glycoside is subjected to ozonolysis to prepare it for conjugation to an amino function of the conjugation partner.

The preferred ozonolytic method is to pass ozone gas into or through a solution of the glycoside in the preferred temperature range for the reaction is −10 to 20° C., for sufficient time for the reaction to reach completion. The time required is dependent on the quantity of material to be ozonolyzed; typically for 100 mg material, the preferred reaction time is 15–30 min.

The concentration of ozone must be sufficient to ozonolyze the substrate, and may be as high as 14 or 15%. The solvents or cosolvents may be any compatible liquids, including water, alcohols, glacial acetic acid, ethyl acetate, methylene chloride, carbon tetrachloride, hexane petroleum ether and dichlorofluoromethane. Water and alcohols, e.g. methanol or ethanol, are preferred. After the reaction, the solution optionally may be purged, e.g., with a stream of nitrogen gas. A reducing agent (e.g., dimethyl sulfide or triphenyl phosphine) or a catalyst may be used to destroy the hydrogen peroxide.

The ozonide is reduced to aldehyde fragments using a suitable reducing agent, e.g., dimethyl sulfide or triphenyl phosphine. The aldehyde byproduct is removed by any suitable means, e.g., column or gel chromatography.

Formation of the Final Conjugate

The hapten aldehyde is reacted with the conjugation partner in the presence of sodium cyanoborohydride or other reducing agents capable of selectively reducing the double board fromed between the aldehyde and an amino group. Preferably, the conjugation is done typically in a buffer at pH 8–9 in the presence of sodium cyanoborohydride (best for proteins) and stirred, all reactants together at room temperature, for 15–20 hours. Protein is purified by repeated dialysis in amicon cell.

The Conjugation Partner

The haptens made by the process of the present invention can be conjugated to carrier proteins and synthetic peptides to be used as antigens cf. Tam. *Proc. Nat. Acad. Sci. USA*, 85, 5409–5413, 1988. The glycoconjugates made are also useful for active specific immunotherapies, and for preparing antibodies against these haptens for inhibiting metastasis.

Through the linking arm, the carbohydrate hapten may be conjugated to a macromolecular carrier, to form a vaccine; to a label, for use in diagnosis; or to a support, for use in diagnosis or in affinity purification.

A macromolecular carrier is a molecule of sufficient size that if a carbohydrate hapten is conjugated to it, the conjugate will elicit an immune response specific to the hapten in an immunized animal. Typically, the carrier will be at least 5,000 daltons molecular weight, more preferably at least 10,000 daltons. The preferred macromolecular carriers are proteins, such as human serum albumin (HSA), bovine serum albumin (BSA), keyhole limpet hemocyanin (KLH), tetanus toxoid, diphtheria toxoid, antibodies, and thyroglobulin. Synthetic peptides, and other synthetic aminated polymers may also have utility. Chitosan may be used.

Several carbohydrate haptens, which are the same or different, may be conjugated to a branched lysine core or other "hub" structure to form an immunogenic conjugate. This is considered the equivalent of hapten-carrier system.

The hapten may also be conjugated to a "label", that is, a molecule capable of participating in a signal producing system. Suitable labels known in the assay arts include enzymes, co-enzymes, enzyme substrates, fluorophores and electron-dense compounds. A conventional label may be derivatized to facilitate the conjugation. The labeled hapten may subsequently be used in a binding assay. The assay may be quantitative or qualitative, heterogeneous or homogenous, and competitive or non-competitive in format.

Alternatively, the hapten may be conjugated to an insoluble support, such as an affinity chromatography or affinity assay support. Suitable supports include Sepharose, latex, red blood cells, polyacrylamide gels, and polystyrene beads. Supports which are not already aminated may be derivatized with amino functions for conjugation purposes.

Synthetic Plans

FIG. 1 illustrates synthesis of various haptens according to the present invention.

In the following examples, which are intended solely for illustration and not for limitation, the numbers of the compounds correspond to those shown in FIG. 1.

EXAMPLES

1. N-Acetyl aD-galactosaminyl-1-O-2-butene 2

Five grams (22.60 mmol) of N-acetyl-D-galactosamine 1 was suspended in 100 mL of crotyl alcohol containing 16 mL of 4M HCl in tetrahydrofuran. The mixture was heated at 50–60° C. with stirring for four hours, and was left at room temperature overnight. The solvent was evaporated, and the remaining yellow solid was purified by silica gel column chromatography eluted with 9:1 chloroform:methanol. The major fraction ($R_f$ 0.18, 9:1 chloroform:methanol) was evaporated to yield 3.36 grams (12.22 mmol, 54%) of a white crystalline solid, $[\alpha]_D^{23°}$+197.8 (c=1, $H_2O$) $^1$H-nmr ($D_2O$) δ:5.90–5.54 (m, 2H, crotyl —CH═CH—), 4.93 (d, 1H, H-1 $J_{1,2}$=3.5 Hz), 4.20–3.70 (m, 9H, other protons), 2.05 (s, 3H, acetamido $CH_3$), 1.70 (d, 3H, J=6.5 Hz, crotyl CH3); $^{13}$C-nmr (D2O ) δ:175.35 (acetamido C═O), 132.64 and 126.72 crotyl —CH═CH—). 96.74 (C-1), 71.76, 69.33, 69.27, 69.55, (C-3, C-4, C-5 and crotyl OCH—), 62.01 (C-6), 50.73 (C-2), 22.76 (acetamido $CH_3$), 17.89 (crotyl $CH_3$).

2. 4, 6-O-Benzylidenyl, N-acetyl aD-galactosaminiyl-1-O-2-butene 3a

Benzaldehyde dimethyl acetal (2.28 g, 14.98 mmol) and 98 mg p-toluenesulfonic acid were added to a suspension of 3.35 g (12.18 mmol) of 2 in 50 mL dry acetonitrile. The mixture was heated at 45° C. for 1.5 hours, and the resulting clear solution was allowed to cool to room temperature before adding 200 mg sodium bicarbonate. The solution was then evaporated to dryness. The residue was taken up in chloroform, and the undissolved material was filtered. The solvent was evaporated, and a white solid remained. This white solid was taken up in a minimum amount of hot ethanol. On cooling, the solution deposited white crystals (3 g, 8.29 mmol, 68%), homogeneous on TLC ($R_f$ 0.57, 9:1 chloroform:methanol); $^1$H-nmr ($CDCl_3$) δ:7.60–7.35 (m, 5H, aromatic), 5.90–5.48 (m, 4H, consisting of crotyl —CH═CH—, benzylidene CH and acetamido NH), 5.00 (d, 1H, H-1, $J_{1,2}$=3.75 Hz), 3.84 (dd, 1H, H-3, $J_{2,3}$=10.5 Hz, $J_{3,4}$=3.0 Hz). 4.58–3.70 (m, 8H, remaining protons), 2.09 (s, 3H, acetamido $CH_3$), 1.75 (d, 3H, J=7.5 Hz, crotyl $CH_3$).

3. 3-O-(2,3,4,6-Tetra-O-acetyl) bD-galactosyl, 4,6-O-benzylidenyl, N-acetyl aD-galactosaminyl-1-O-2-butene 7

After 50 mL of solvent was distilled from a mixture of 2.09 g (8.27 mmol) mercuric cyanide, 125 mL dry nitromethane and 125 mL of dry benzene, 2 g (5.5 mmol) of 3 was added and the reaction flask was sealed with a serum cap. The reaction flask was flushed with a stream of dry nitrogen gas for ten minutes before heating to 60° C. A solution of 3.4 g (8.27 mmol) of acetobromogalactose in 20 mL dry nitromethane was then added over a period of one hour by standard syringe technique. After overnight stirring, an additional batch of 1.4 g (5.54 mmol) mercuric cyanide and a solution 2.26 g (5.49 mmol) acetobromogalactose in 20 mL dry benzene was added. The reaction mixture was again stirred overnight at 60° C. After the mixture was cooled to a room temperature, the mixture was washed successively with saturated sodium bicarbonate solution, 30% potassium bromide solution, and saturated sodium chloride solution. Each extraction was followed by back extraction of the aqueous layer with chloroform. The combined organic layer was dried with anhydrous magnesium sulfate before evaporation to dryness. The residue was applied to a column of silica gel eluted progressively with 6:4, 7:3, then 8:2 ethyl acetate:hexane to obtain a fraction with $R_f$ 0.33 on TLC eluted with 8:2 ethyl acetate:hexane. Evaporation of the fraction yielded 3.41 g (4.92 mmol, 89%) of a foam; $^1$H-nmr ($CDCl_3$) δ:7.65–7.32 (m, 5H, benzylidene aromatic protons), 5.80–3.62 (m, 19H, remaining 30 proton), 4.74 (d, 1H, H-1', $J_{1,2}$=8.0 Hz), 2.20–1.95 (m, 15H, acetyl $CH_3$), 1.72 (d, 3H crotyl $CH_3$).

4. 3-O-bD-Galactosyl, N-acetyl aD-galactosaminyl-1-O-2-butene 9

The disaccharide 7, (2.9 g, 4.18 mmol) was taken up in 40 mL of 80% acetic acid and heated at 60° C. for two hours. The resulting solution was evaporated to dryness. After the residue had been dried under high vacuum overnight, it was taken up in methanol. A solution of sodium methoxide was added dropwise until the pH reached about 9.0. After stirring at room temperature for 0.5 hours, the solution was neutralized with IR-120 (H) resin. The solvent was evaporated and a white solid remained, which was taken up in water and washed twice with ethyl acetate.

The aqueous layer was lyophilized to yield a white solid, which was applied to a P-2 column eluted with water. Lyophilization of the main fraction gave 1.3 g (2.97 mmol, 71%) of white solid, which is homogeneous on TLC ($R_f$ 0.56, 65:35:5 chloroform:methanol:water), $[\alpha]_D$+117.6 (C=1, $H_2O$); $^1$H-nmr ($D_2O$) δ:5.76 (m,2H,crotyl —CH═CH—), 4.74 (d, 1H, H-1, $J_{1,2}$=3.5 Hz), 4.26 (d, 1H, H-1', $J_{1,2}$=7.5 Hz) 4.20–3.30 (m, 14H remaining protons), 1.90 (s, 3H, acetamido CH3) 1.55 (d, 3H, crotylmethyl)

5. 3-O-Benzoyl, 4,6-benzylidenyl, N-acetyl aD-galactosaminyl-1-O-2-butene 3c

Benzoyl chloride (5.6 g) was added dropwise to a solution of 9.9 grams pyridine in 100 mL dichloromethane. The resulting slightly pink solution was added dropwise to a solution of 4.73 g (13.02 mmol) of the benzylidene compound 3a dissolved in 250 mL dry dichloromethane cooled to 0° C. After stirring at room temperature for one hour, the resultant reaction mixture was washed with 200 mL saturated sodium bicarbonate solution and 200 mL saturation sodium chloride solution. After drying with magnesium sulfate, the solution was concentrated and again co-evaporated wit toluene to yield a white solid. The solid was dissolved in ethyl acetate to which hexane was added until turbidity persisted. This mixture was kept at −4° C. for either one day or until a crop of crystals deposited (6.0 g, 12.88 mmol, 99%).

$^1$H-nmr ($CDCl_3$) δ:8.20–7.35 (m, 10H, aromatic protons), 5.80 (m, 1H, crotyl proton), 5.50 (s, 1H, benzylidene CH) 5.39 (dd, 1H, H-3, $J_{3,4}$=3.2 Hz, $J_{2,3}$=11.5 Hz) 5.06 (d, 1H, H-1, $J_{1,2}$=3.5 Hz), 4.97 (ddd, 1H, H-2), 4.47 (bd, 1H, H-4, $J_{3,4}$=3.0 Hz, $J_{4,5}$=1 Hz), 4.30 (dd, 1H, H-6A, $J_{5,6}$=1.5 Hz), 3.99(m, 1H, crotyl-CH—$_2$—), 3.82 (m, 1H, crotyl —CH—$_2$—), 1.75 (d, 3H, crotylmethyl).

6. 3-O-Benzoyl, N-acetyl aD-galactosaminyl-1-O-2-butene 4b

Six grams (12.83 mmol) of the benzoate 3c was dissolved in 50 mL of 80% acetic acid and heated at 60° C. for one hour. The solution was evaporated to near dryness and was subsequently co-distilled with toluene to yield a white solid. The solid was recrystallized from ethyl acetate:hexane to give 4 g (10.55 mmol, 82%) of crystals.

$^1$H-nmr ($CDCl_3$) δ:8.05–7.30 (m, 5H, aromatic), 5.90 (d, 1H, NH, $J_{2,NH}$=8.0 Hz), 5.85–5.50 (m, 2H, crotyl protons), 5.25 (dd, 1H, H-3, $J_{3,4}$=3.0 Hz, $J_{2,3}$=10.8 Hz), 4.90 (d, 1H, H-1, $J_{1,2}$=3.5 Hz), 4.85 (m, 1H, H-2), 4.30–3.20 (m, 8H, other protons), 1.90 (s, 3H, acetyl $CH_3$), 1.75 (d, 3H, crotyl $CH_3$).

7. 3-O-Benzoyl, 6-O-(methyl, 4, 7,8,9-tetra-O-acetyl) a sialyl, N-acetyl aD-galactosaminyl-1-O-2-butene 5b Methyl,4,7,8,9-tetra-O-acetyl, sialyl-2-chloride (300 mg, 0.59 mmol) (A. Marra and P. Sinay, Carbohydr. Res. 190: 317–322, 1989) in 2 mL dichloromethane was added dropwise to a stirred mixture of 400 mg (1.06 mmol) of the diol 4b, 1.8 g of powdered 4 Å molecular sieve, and 215 mg (0.84 mmol) silver trifluoromethane-sulfonate in 5 mL dichloromethane over a period of one hour while cooling at −10° C. The mixture was stirred overnight at room temperature and then diluted with 10 mL of dichloromethane. The solid was filtered. The filtrate was washed with saturated sodium bicarbonate solution and saturated sodium chloride solution before being dried with anhydrous sodium sulfate. The solid was filtered, and the solution was evaporated to dryness and applied to a column of silica gel eluted with 8:2:0.2 ethyl acetate:hexane:methanol. The fractions corresponding to $R_f$=0.12 were combined and again chromatographed on a silica gel column eluted with 20:1 chloroform:methanol. The 30 fractions corresponding to $R_f$=0.21 yeilded 86 mg, (0.1 mmol, 17%) as a colourless solid.

$^1$H-nmr (CDCl$_3$) δ:8.15–7.40 (m, 5H, aromatic), 5.85–5.50 (m, 2H, crotyl proton), 5.73 (d, 1H, NH), 5.46 (d, 1H, NH), 5.28 (dd, 1H, H-3, $J_{2,3}$=11.0 Hz, $J_{3,4}$=3.0 Hz), 5.40–3.70 (m, other protons), 3.80 (s, 3H, CO$_2$CH$_3$), 3.00 (d, 1H, OH), 2.60 (dd, 1H, H-3'e, J=4.5 Hz and 12.5 Hz), 2.13, 2.11, 2.01, 1.97, 1.87, 1.86 (6s, 18H, acetyl and acetamido methyl protons), 1.75 (d, 3H, crotyl CH$_3$)

8. 6-O-a Sialyl, N-acetyl aD-galactosaminyl-1-O-2-butene 6

The blocked disaccharide 5b (38 mg, 0.045 mmol) in 5 mL of methanol was treated with 700 μL of 0.1 N NaOH overnight. The solution was then treated with Amberlite resin IR-120 (H+) After the resin was filtered, the filtrate was evaporated to dryness. The residue was again taken up in 2 mL water and washed three times with 2 mL chloroform. The aqueous layer was lyophilized to form 26 mg of a foamy solid (0.045 mmol, 100%)

$^1$H-nmr (D$_2$O) δ: 5.90–5.55 (m, 2H, olifinic protons), 4.90 (d, 1H, H-1, $J_{1,2}$=3.5 Hz), 4.20–3.55 (m, 15H, other protons), 2.74 (dd, 1H, H$_3$e, J=4.5 and 12.5 Hz), 2.05 (s, 6H, acetamido methyl proton), 1.72 (d, 3H, crotyl methyl protons), 1.67 (t, 1H, H$_3$a, J=12.5 Hz); $^{13}$C-nmr (D$_2$O) d:175.19, 174.68, 173.54 (C=O), 132.14, 126.07, (crotyl double bond), 100.58 (C-2'), 96.04 (C-1), 15 72.74, 71.91, 69.64, 68.79, 68.67, 68.37, 67.72, 63.86, 62.81, 52.06, 50.03 (C-2), 40.46, (C-3 ), 22.25, 22.16, (2×N-acetyl) 17.34 (crotyl methyl).

9. 3-O-(2,3,4,6-Tetra-O-acetyl) bD-galactosyl, N-acetyl aD-galactosaminyl-1-O-2-Butene 8

The disaccharide 7 (2 g, 2.88 mmol) was taken up in 40 mL 80% acetic acid and heated at 60° C. for two hours. The solution was evaporated to dryness. The syrupy residue was applied to a column, eluted with 9:1 chloroform:methanol and the main fraction ($R_f$=0.2, 9:1 chloroform: methanol) was collected and evaporated to yield 1.05 g (2.40 mmol, 83%).

$^1$H-nmr (CDCl$_3$) δ:5.75 (m, 1H, crotyl proton), 5.62–3.72 (m-19H, remaining protons), 2.90–2.60 (m, 2H, OH protons), 2.20–2.00 (m, 15H, acetyl CH$_3$), 1.72 (d, 3H, crotyl CH$_3$).

10. 3-O-(2,3,4,6-Tetra-O-acetyl) bD-galactosyl, 6-O-(methyl-4,7,8,9-tetra-O-acetyl) a sialyl, N-acetyl aD-galactosaminyl-1-O-2-butene 10

Methyl, 4,7,8,9-tetra-O-acetyl, sialyl-2-chloride- (0.5 g, 0.98 mmol) in 4 mL dichloromethane was added dropwise to a stirred mixture of 0.5 g of the diol 7 (1.14 mmol), 3 g powdered 4 Å molecular sieve and 0.358 g (1.39 mmol) silver trifluoromethane sulfonate in 10 mL dichloromethane over a period of 45 minutes while cooling at –10° C. The mixture was stirred at room temperature for two days. The solid was filtered and the solution was washed with saturated sodium bicarbonate solution and then with sodium chloride solution. The organic layer was dried with magnesium sulfate and evaporated to dryness. The residue was taken up in 95% ethanol and applied to a LH-20 column eluted with the same solvent. The first fraction that was collected showed two spots on TLC ($R_f$=0.33 and 0.23, 9:1 chloroform:methanol). The second fraction was evaporated and the residue was applied to a column of silica gel first eluted with 50:1 and then 20:1 chloroform:methanol. The lower spot (215 mg, 0.2 mmol, 20% yield) eluted was collected.

$^1$H-nmr (CCl$_3$) δ: 5.81–5.75 (m, 1H, crotyl CH=CH), 5.61–5.50 (m, 2H, crotyl CH=CH and NH), 5.42–5.32 (m 3H), 5.35–5.14 (m, 2H) 5.05–4.95 (dd, 1H, J=3.11, J=11.5 Hz, H-3), 4.91–4.84 (m, 1H), 4.82- (d, 1H, J=3.5 Hz, H-1), 4.64–4.61 (d, 1H, J=8.0 Hz, H-1'), 4.62–4.52 (m, 1H), 4.34–4.28 (dd, 1H, J=3.5 Hz, J=12.0 Hz, H-2), 4.22–3.98 (m, 7H), 4.95–3–84 (m, 4H), 3.82 (s, 3H COOCH3) 3.78–3.73 dd, (1H, J=3.0 Hz, J=10.0 Hz, H-2'), 3.64–3.60 (m, 1H), 2.55–2.58 (dd, 1H, J=4.5 Hz, J=12.5 Hz, H-3 eq), 2.55–5.52 (bs 1M, 4-OH), 2.20–1.98 (m, 19H, 6× OAc, 2× NHAc, H-3 Hax) and 1.75 (d, 3H, crotyl CH3).

11. 3-O-bD-Calactosyl, 6-O-a sialyl, N.-acetyl aD-galactosaminyl-1-o-2-butene 11

The blocked trisaccharide 10 Compound (180 mg, 0.17 mmol) was dissolved in 10 mL of methanol to which was added 10 mL of 0.1 N sodium hydroxide solution. The reacton mixture was left at room temperature for two days. The solution was then treated with IR-120 (H) resin until the pH of the solution becomes acidic. The solution was filtered and freeze dried. The residue was applied to a P-2 biogel column and eluted with water. The main fraction collected was lyophilized to yeild 50 mg of a white powder.

$^1$H-nmr (D2O) δ: 5.91–5.78 (m, 1H, crotyl CH=CH), 5.67–5.57 (m, 1H, crotyl CH=CH), 4.92–4.85 (d, 1H, J=4.0 Hz, H-1), 4.47–4.42 (d, 1H, J=8.0 Hz, H-1'), 4.33–4.24 (m, 2H), 4.18–3.47 (m, 19H), 2.76–2.69 (dd, 1H, J=4.5 Hz, J=12.5 Hz, H-3 eq) 2.3–2.1 (2s, 6H, 2× NCOCH3), and 1.73–1.63 (m, 4H, crotyl-CH3, H-3 ax) $^{13}$C-nmr 96.84 (C-1), 101.25 (C-2") 105.56 (C-1'). 126.75 (CH=CH), and 132.80 (O—CH=CH).

General Method of Ozonolysis

To form an aldehyde which can be conjugated to a protein, a stream of ozone gas is passed through an aqueous solution of a compound having a linker arm derived from an unsaturated alcohol, such as crotyl alcohol.

A stream of ozone gas was passed through a solution of hapten containing an olifinic aglycon in distilled water cooled to 0° C. for about four to 10 minutes, with stirring. The reaction was monitored by thin layer chromatography using a solvent system of 65:35:5 of chloroform:Methanol::water. After the reaction proceeded to completion, the reaction was allowed to warm to room temperature over a period of one half hour, with stirring, followed by purging with a stream of nitrogen gas for fifteen minutes to expel traces of ozone and most of the fragment aldehyde, eg. acetaldehyde. One drop of dimethyl sulfide was added to the solution, to break down the ozonide and to destroy any trace of peroxides formed during ozonolysis, which was then washed twice with diethyl ether. A stream of nitrogen gas was again passed through the aqueous solution for 30 to 40 minutes.

This process removes any traces of ozone or aldehyde left in the solution. This solution was directly used for conjugation to a protein.

Conjugation to Protein

The ozonolyzed haptens as prepared above can be directly conjugated to any desired proteins, polypeptides, or synthetic proteins. The process of conjugation is direct and produces byproducts which can be disposed of safely.

Haptens as ozonolyzed as above were conjugated to human serum albumin and to keyhole limpet hemocyanin. To conjugate the hapten to human serum albumin, the ozonolyzed hapten was added to human serum albumin in a ratio of 1.2:1:1 weight/weight of hapten:sodium cyanoborohydride:protein. The reaction was carried in a phospate buffer, pH 8.0–9.0, and the reaction was allowed to go to completion at room temperature for about 16 hours. Depending upon the hapten used, the reaction time is from approximately 10 to 30 hours. The conjugate was purified by ultrafiltration using Amicon PM10 membrane. The neutral sugar content was determined by the phenol-sulfuric acid method (M. Dubois et. al., *Anal. Chem.*, 28: 350–356, 1956) and the sialic acid content was determined by the diphenylamine method of Niazi et. al., *Cancer Res.*, 8: 653, 1948.

To conjugate the hapten to keyhole limpet hemocyanin, the ozonolyzed hapten was added to keyhole limpet hemocyanin in a ratio of 1.8:1:1 weight/weight hapten:sodium cyanoborohydride:protein. The reaction was conducted in phosphate buffer, pH 8.0–9.0, and the reaction was allowed to go to completion at room temperature for about 20 hours. The conjugate was purified by ultrafiltration using an Amicon PM10 membrane. The neutral sugar content was determined by the phenol-sulfuric acid method (M. Dubois et. al., *Anal. Chem.*, 28: 350–356, 1956) and the sialic acid content was determined by the diphenylamine method of Niazi et. al., *Cancer Res.*, 8: 653, 1948.

Conjugation to Synthetic Peptides

Fifty milligrams of TFa-O-crotyl in 5 mL of distilled water was ozonolyzed by passing a stream of ozone gas through the solution cooled to 0° C. for ten minutes with stirring. The completion of the reaction was assayed by thin layer chromatography using 65:35:5 chloroform:methanol:water. Nitrogen gas was then bubbled through the solution to purge the remaining ozone gas in the reaction mixture. Approximately 10 mg of freshly distilled dimethyl sulfide was then added and the solution was stirred at room temperature for 30 minutes. The dimethyl sulfide reduced the initially formed ozonide to the aldehyde fragments. The aqueous solution was then concentrated by evaporation to remove the acetaldehyde by-product. The TFa-O-acetaldehyde solution, about 2 mL, was added to a solution of 10 mg of the hexadecavalent lysine cluster obtained according to Posnett et. al., in *J. Biol. Chem.*, 263: 1719, 1988, in 10 mL borate buffer pH 8.5. After ten minutes of stirring, 30 mg of sodium cyanoborohydride was added and stirring was continued for about 16 hours. The TFa-clustered lysine was purified to a fraction homogeneous on a LH-20 column by eluting with 1:1 ethanol:water. The solution was again ultrafiltered using YM2 membrane filter to remove small molecules such as unreacted carbohydrate and sodium cyanoborohydride. Filtration was repeated by adding 10 mL distilled water twice. The material was lyophilized to obtain 10 mg of white solid. Carbohydrate analysis was performed using the phenol-sulfuric acid method.

The cluster contained eight molecules of TFa haptens per mol of the cluster.

Vaccine

STn-crotyl (6-O-a-sialyl, agalNAc-O-crotyl) was produced as above. This is a synthetic mimic of the natural O-linked epitope on mucins, 6-O-a-sialyl, agalNAc-O-serine (STn-Serine). STN crotyl was conjugated to the carrier protein KLH through the hydroxyacetaldehyde linker arm as described above, and a "vaccine" containing STn-KLH plus DETOX__ adjuvant was formulated.

DETOX__ is available from RIBI ImmunoChem Research Inc., Hamilton, Mont., and is formulated as a lyophilized oil droplet emulsion containing monophosphyrl lipid A and cell wall skeleton for *Mycobacterium phlei*.

The vaccine as prepared above was evaluated in BALB/c mice and in metastatic breast cancer patients. The specificity and titres of IgG antibodies were evaluated by ELISA on ovine submaxillary mucin (OSM) solid phases, as OSM is a convenient source of repeating, natural O-linked STN-serine structures. Mice immunized three times with as little as 0.25 $\mu$g of STN-KLH produced a median IgG titre of over 1:5000 on solid phase OSM. An animal model was studied with Ta3Ha Cell line which is a murine mammary carcinoma that expresses TF anigens. TF antigens generated excellent immune response and protected the mice that were given the TA3Ha cell line as challenge while control group died within three weeks. STN is already in human clinical trials which demonstrated the partial responses, in terms of tumor regression following STN specific immune response.

| | Table of Compounds |
|---|---|
| 1a | N-Acetyl-D-galactosamine |
| 2 | N-Acetyl $\alpha$D-galactosaminyl-1-O-2-butene |
| 3a | 4,6-O-Benzylidenyl, N-acetyl $\alpha$D-galactosaminyl-1-O-2-butene |
| 3b | 3-0-Acetyl, 4,6-O-benzylidenyl, N-acetyl $\alpha$D-galatosaminyl-1-O-2-butene |
| 3c | 3-O-Benzoyl, 4,6-O-benzylidenyl, N-acteyl $\alpha$D-galactosaminyl-1-O-2-butene |
| 4a | 3-O-Acetyl, N-acetyl $\alpha$D-galactosaminyl-1-O-2-butene |
| 4b | 3-O-Benzoyl, N-acetyl $\alpha$D-galactosaminyl-1-O-2-butene |
| 5a | 3-O-Acetyl, 6-O-(methyl,4,7,8,9-tetra-O-acetyl) $\alpha$ sialyl, N-acetyl $\alpha$-galactosaminyl-1-O-2-butene |
| 5b | 6-O-Benzoyl, 6-O-(methyl,4,7,8,9-tetra-O-acetyl) $\alpha$ sialyl, N-acetyl $\alpha$D-galactosaminyl-1-O-2-butene |
| 6 | 6OO-$\alpha$ Sialyl, N-acetyl $\alpha$D-galactosaminyl-1-O-2-butene |
| 7 | 3-O-(2,3,4,6-Tetra-O-acetyl) $\beta$D-galactosyl, N-acetyl $\alpha$D-galactosaminyl-1-O-2-butene |
| 8 | 3-O-(2,3,4,6-Tetra-o-acetyl) $\beta$D-galactosyl, N-acetyl $\alpha$D-galactosaminyl-1-O-2-butene |
| 9 | 3-O-$\beta$D-Galactosyl, N-acetyl $\alpha$D-galactosaminyl-1-O-2-butene |
| 10 | 3-O-(2,3,4,6-Tetra-O-acetyl) $\beta$D-galactosyl,6-O-(methyl,4,7,8,9-tetra-O-acetyl) $\alpha$ sialyl, N-acetyl $\alpha$D-galactosaminyl-1-O-2-butene |
| 11 | 3-O-$\beta$D-Galactosyl, 6-O-$\alpha$ sialyl, N-acetyl $\alpha$D-galactosaminyl-1-O-2-butene |
| 12 | 6-O-$\alpha$ Sialyl, N-acetyl $\alpha$D-galactosaminyl-1-O-2-acetyladehyde |
| 13 | Acetobromogalactose |
| 14 | 3,4,6-Tri-O-acetyl, 1-galactal |
| 15 | 2-Azido, 3,4,6-Tri-O-acetyl, 1-galactal |
| 16 | 2-Azido, 3,4,6-Tri-O-acetyl, $\alpha$D-galactosyl-1-O-2-butene |
| 17 | 2-Acetamido, 3,4,6, tri-O-acetyl, galactose oxycarbonium ion |
| 18 | 4,5(3,4,6-Tri-O-acetyl, D galactosyl) 2-methyl-1,3 oxazoline |
| 19 | 2-O Substituted acetaldehyde |
| 20 | Reduced Schiff's base |
| 21 | Shiff's Base |
| 22a | Allyl alcohol |
| 11b | Crotyl alcohol |
| 22c | 3-Methyl, 2-butenol |
| 22d | 3-Phenyl, 2-propenol |
| 22e | 2-O-Allyl, ethanol |
| 22f | 2-O-Crotyl, ethanol |
| 22g | 5-O-Allyl, pentanol |
| 22h | 5-O-Crotyl, pentanol |
| 23 | N-Acetyl $\alpha$D-galactosaminyl-1-O-5(5'-O-allyl) pentane |
| 24 | 3-O-$\beta$D-Galactosyl, N-acetyl $\alpha$D-galactosaminyl-1-O-(10'-O-crotyl) decane |
| 25 | 6-O-$\alpha$ Sialyl, N-acetyl $\alpha$D-galactosaminyl-1-O{6'-O'(3" phenyl) propenyl} hexane |
| 26 | 6-O-$\alpha$ Sialyl, N-acetyl $\alpha$D-galactosaminyl-1-O{5'-O-(2" oxo) ethyl} pentane |
| 27 | General formula for the linker arm. |
| 28 | TN Hapten witha general linker arm. |
| 29a | Sialyl TN - general linker arm. |
| 29b | Glycolyl sialyl - TN with a general liner arm. |
| 30 | TF with a general linker arm. |
| 31a | STF with general linker arm. |
| 31b | Glycolyl STF with general linker arm. |

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A method for covalently linking a saccharide to a carrier molecule containing at least one primary amino group comprising:
   reacting said saccharide in an acid medium, with an unsaturated alcohol having a non-terminal double bond;
   ozonolyzing said saccharide-alcohol to form a hapten-glycoside carbonyl derivative;
   reductively aminating said glycoside carbonyl compound to link said glycoside to said carrier molecule.

2. The method according to claim 1 further comprising removing carbonyl compound formed when said glycoside carbonyl derivative is reductively aminated.

3. The method according to claim 1 wherein the carrier molecule is selected from the group consisting of proteins and polypeptides.

4. The method according to claim 3 wherein said carrier molecule is selected from the group consisting of keyhole limpet hemocyanin, human serum albumin, and bovine serum albumin.

5. The method according to claim 1 wherein said saccharide is selected from the group consisting of sialyl Tn, Tn, Tα, and sialyl-2–6Tα.

6. The method according to claim 1 wherein said saccharide is selected from the group consisting of lacto series type 1 chains, lacto series type 2 chains, cancer-associated ganglio chains, globotriose, globotetraose, globopentaose, isoglobotriose, isoglobotetraose, mucotriose, mucotetraose, lactotriose, lactotetraose, neolactotetraose, gangliotriose, gangliotetraose, galabiose, and 9-O-acetyl-GD3.

7. The method according to claim 1 wherein said saccharide is selected from the group consisting of sialyl-Lea and sialyl Lex.

8. The method according to claim 5 wherein the saccharide is N-acetylgalactosamine.

9. The method according to claim 1 wherein the unsaturated alcohol has the formula:

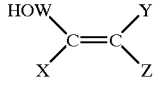

wherein W is $(CH_2)_n$ and n is from 1–20;
X, Y and Z are $(CH_2)_m H$ wherein m is from 1 to 5, with the proviso that X, Y and Z cannot all be H.

10. The method according to claim 9 wherein the alcohol is selected from the group consisting of crotyl alcohol, 3-methyl-but-2-en-1-ol, 3-methyl-pent-2-en-1-ol, 3-ethyl-pent-2-en-1-ol, pent-2-en-1-ol, hex-2-en-1-ol, and 4-methyl-hex-2-en-1-ol.

11. A method of preparing an alpha olefinic glycoside which comprises reacting a carbohydrate with an unsaturated alcohol, in an acid medium, to create an alpha-glycosidic linkage between the carbohydrate and the alcohol where the only solvent for said reaction is said unsaturated alcohol.

12. The method of claim 11 wherein the carbohydrate has the formula X—Y where X is N-acetylgalactosamine and Y is at least one saccharide unit and the linkage is between the N-acetylgalactosamine and the alcohol.

13. The method of claim 11 in which the acid concentration is adjusted so that the yield of the alpha olefinic glycoside is at least 50%.

14. The method of claim 11 in which the carbohydrate is selected from the group consisting of Tn, sialyl Tn, FT, and Sialyl TF.

15. The method of preparing a carbohydrate hapten-linking arm conjugate with an alpha glycosidic linkage between the hapten and the linking arm which comprises preparing an alpha olefinic glycoside according to the method of claim 11 by reacting the carbohydrate hapten with an unsaturated alcohol, and ozonolyzing the glycoside to generate a conjugate of the carbohydrate hapten with a linking arm derived from said alcohol.

16. A method of preparing a artificial carbohydrate epitope-bearing immunogen which comprises preparing a carbohydrate hapten-linking arm conjugate by the method of claim 15, and then reacting the conjugate through said linking arm with an immunogenic carrier to form an artificial carbohydrate epitope-bearing immunogen.

17. A method for preparing an alpha olefinic glycoside which consists essentially of reacting a carbohydrate with an unsaturated alcohol, in an acid medium, to create an alpha-glycosidic linkage between the carbohydrate and the alcohol.

18. The method according to claim 11 wherein the reaction is conducted in the presence of hydrochloric acid as the acid medium and the concentration of hydrochloric acid is present in a concentration of about 4.8 mole %.

19. The method of claim 11 in which the acid concentration in the medium is from 1.5 to 6.0 mole %.

20. A method of preparing an alpha olefinic glycoside which comprises reacting a carbohydrate with an unsaturated alcohol, in an acid medium, to create an alpha-glycosidic linkage between the carbohydrate and the alcohol, and in which the acid concentration in the medium is from 1.5 to 6.0 mole %.

21. The method of preparing a carbohydrate hapten-linking arm conjugate with an alpha glycosidic linkage between the hapten and the linking arm which comprises preparing an alpha olefinic glycoside according to the method of claim 18 by reacting the carbohydrate hapten with an unsaturated alcohol, and ozonolyzing the glycoside to generate a conjugate of the carbohydrate hapten with a linking arm derived from said alcohol.

22. The method of claim 1 in which the only solvent for the reaction of the saccharide with the unsaturated alcohol is the unsaturated alcohol.

23. The method of claim 1 in which the acid concentration in said medium is from 1.5 to 6.0 mole %.

* * * * *